United States Patent
Cheung et al.

(10) Patent No.: US 9,598,729 B2
(45) Date of Patent: Mar. 21, 2017

(54) MODIFIED RNASE H AND DETECTION OF NUCLEIC ACID AMPLIFICATION

(71) Applicant: SAMSUNG TECHWIN CO., LTD., Changwon (KR)

(72) Inventors: Win Den Cheung, Olney, MD (US); Jason Opdyke, Silver Spring, MD (US)

(73) Assignee: Hanwha Techwin Co., Ltd., Changwon-si (KR)

( * ) Notice: Subject to any disclaimer, the term of this patent is extended or adjusted under 35 U.S.C. 154(b) by 0 days.

(21) Appl. No.: 14/064,719

(22) Filed: Oct. 28, 2013

(65) Prior Publication Data

US 2014/0087968 A1 Mar. 27, 2014

Related U.S. Application Data

(62) Division of application No. 13/108,311, filed on May 16, 2011, now Pat. No. 8,618,253.

(Continued)

(51) Int. Cl.
  *C12Q 1/68* (2006.01)
  *C12P 19/34* (2006.01)
  *C12N 9/22* (2006.01)

(52) U.S. Cl.
  CPC .............. *C12Q 1/686* (2013.01); *C12N 9/22* (2013.01); *C12Q 1/6848* (2013.01)

(58) Field of Classification Search
  CPC  C12Q 1/6848; C12Q 1/686; C12Q 2521/327; C12N 9/22
  See application file for complete search history.

(56) References Cited

U.S. PATENT DOCUMENTS 5,338,671 A    8/1994  Scalice
5,677,152 A *  10/1997 Birch .................. C12N 9/1252
                                                              435/6.12

(Continued)

FOREIGN PATENT DOCUMENTS

CN          1151437 A     6/1997
EP          0771870 A1    5/1997

(Continued)

OTHER PUBLICATIONS

Intellectual Property Office of P.R. China, Communication dated Apr. 28, 2014, issued in counterpart Chinese Patent Application No. 201180026040.8.

(Continued)

*Primary Examiner* — Young J Kim
(74) *Attorney, Agent, or Firm* — Sughrue Mion, PLLC

(57) ABSTRACT

A reversibly modified 'hot start' RNase H enzyme composition is described for the improved CATACLEAVE™ probe detection of nucleic acid sequences in a test sample. A key feature of the enzyme composition is the ability to regulate the catalytic activity of the RNase H during the course of a reverse transcription-PCR cycle. Thus, RNase H activity can be initially suppressed to minimize degradation of RNA: DNA primer heteroduplexes prior to reverse transcription. After cDNA synthesis is complete, RNase H activity is induced to promote the cleavage and fluorescent detection of CATACLEAVE™ probes that anneal to target DNA sequences within the reverse transcriptase-PCR products. The inducible RNase H enzyme is amenable to high throughput applications requiring one step reverse transcriptase CATACLEAVE™ PCR in a single reaction mix.

21 Claims, 14 Drawing Sheets

Related U.S. Application Data

(60) Provisional application No. 61/347,984, filed on May 25, 2010.

(56) References Cited

U.S. PATENT DOCUMENTS

| | | | | |
|---|---|---|---|---|
| 5,853,990 | A | * | 12/1998 | Winger et al. ............... 435/6.18 |
| 6,951,722 | B2 | | 10/2005 | Mukai et al. |
| 8,008,055 | B2 | * | 8/2011 | Uemori ................... C12N 9/22 435/183 |
| 8,119,336 | B2 | * | 2/2012 | Sampath et al. .................. 435/5 |
| 2009/0325169 | A1 | * | 12/2009 | Walder ................ C12Q 1/6844 435/6.18 |

FOREIGN PATENT DOCUMENTS

| | | |
|---|---|---|
| EP | 0962526 A2 | 12/1999 |
| JP | 2000-004878 A | 1/2000 |
| WO | 2005/123913 A3 | 12/2005 |
| WO | 2009/135093 A2 | 11/2009 |

OTHER PUBLICATIONS

Maeder DL et al., "ribonuclease HII [Pyrococcus furiosus DSM 3638]," GenBankAccession, May 5, 2010, No. NP_579510, 1 page.

Kitabayashi, Masao et al., "Improvement of Reverse Transcription PCR by RNase H," Graduate School of Biosphere Sciences, Hiroshima University, Biosci. Biotechnol. Biochem., Nov. 30, 2013, vol. 67, No. 11, pp. 2474-2476.

European Patent Office, Communication issued Nov. 12, 2013 in a counterpart European Application No. 11786887.7.

Rait, et al.; "Modeling Formalin Fixation and Antigen Retrieval with Bovine Pancreatic Ribonuclease A: I—Structural and Functional Alterations," Laboratory Investigation, Feb. 2004, vol. 84, 8 pages total.

Fowler, et al.; "Modeling Formalin Fixation and Histological Processing with Ribonuclease A: Effects of Ethanol Dehydration on Reversal of Formaldehyde Cross-Links," Laboratory Investigation, Jul. 2008, vol. 88, 7 pages total.

Japanese Patent Office, Communication dated Feb. 2, 2015, issued in counterpart Japanese Application No. 2013-512536.

Japanese Patent Office, Communication dated Jan. 8, 2016, issued in corresponding Japanese Patent Application No. 2013-512536.

Harvey J.J. et al., "Characterization and applications of CataCleave probe in real-time detection assays", Analytical Biochemistry, 2004, pp. 246-255.

Takahashi K., "The Structure and Function of Ribonuclease T1", J. Biochem., 1977, vol. 81, No. 3, pp. 641-646.

\* cited by examiner

SEQUENCE LISTING

```
<160> NUMBER OF SEQ ID NOS: 19

<210> SEQ ID NO 1
<211> LENGTH: 224
<212> TYPE: PRT
<213> ORGANISM: Pyrococcus furiosus

<400> SEQUENCE: 1

Met Lys Ile Gly Gly Ile Asp Glu Ala Gly Arg Gly Pro Ala Ile Gly
1               5                   10                  15

Pro Leu Val Val Ala Thr Val Val Asp Glu Lys Asn Ile Glu Lys
            20                  25                  30

Leu Arg Asn Ile Gly Val Lys Asp Ser Lys Gln Leu Thr Pro His Glu
        35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
    130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220

<210> SEQ ID NO 2
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (1)..(1)
<223> OTHER INFORMATION: 5'- end is coupled to FAM
<220> FEATURE:
<221> NAME/KEY: misc_RNA
<222> LOCATION: (10)..(13)
<223> OTHER INFORMATION: RNA sequence
<220> FEATURE:
<221> NAME/KEY: modified_base
<222> LOCATION: (22)..(22)
```

```
<223> OTHER INFORMATION: 3'-end is coupled to Iowa Black

<400> SEQUENCE: 2
tctggttgau uucctgatcg ca                                             22

<210> SEQ ID NO 3
<211> LENGTH: 22
<212> TYPE: DNA
<213> ORGANISM: Artificial Sequence
<220> FEATURE:
<223> OTHER INFORMATION: oligonucleotide

<400> SEQUENCE: 3
tgcgatcagg aaatcaacca ga                                             22

<210> SEQ ID NO 4
<211> LENGTH: 19
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (1)..(1)
<223> OTHER INFORMATION: 5" end is coupled to FAM
<220> FEATURE:
<221> NAME/KEY: misc_RNA
<222> LOCATION: (8)..(11)
<223> OTHER INFORMATION: RNA sequence
<220> FEATURE:
<221> NAME/KEY: modified_base
<222> LOCATION: (19)..(19)
<223> OTHER INFORMATION: 3" end is coupled to Iowa Black

<400> SEQUENCE: 4
cgatcaggaa atcaaccag                                                 19

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tcgtcattcc attacctacc                                                20

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
tactgatcga taatgccaga cgaa                                           24

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ccaaggggaa gtgacatagc aggaactact                                     30
```

```
<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
ctgacgacag ggctatacat tcttactatt t                              31

<210> SEQ ID NO 9
<211> LENGTH: 27
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (1)..(1)
<223> OTHER INFORMATION: 5" end is coupled to FAM
<220> FEATURE:
<221> NAME/KEY: misc_RNA
<222> LOCATION: (10)..(13)
<223> OTHER INFORMATION: RNA sequence
<220> FEATURE:
<221> NAME/KEY: modified_base
<222> LOCATION: (27)..(27)
<223> OTHER INFORMATION: 3" end is coupled to Iowa Black

<400> SEQUENCE: 9 taccctttcag gaacaaatag gatggat                                  27

<210> SEQ ID NO 10
<211> LENGTH: 16
<212> TYPE: PRT
<213> ORGANISM: Pyrococcus furiosus

<400> SEQUENCE: 10

Gly Ile Asp Glu Ala Gly Arg Gly Pro Ala Ile Gly Pro Leu Val Val
1               5                   10                  15

<210> SEQ ID NO 11
<211> LENGTH: 12
<212> TYPE: PRT
<213> ORGANISM: Pyrococcus furiosus

<400> SEQUENCE: 11

Leu Arg Asn Ile Gly Val Lys Asp Ser Lys Gln Leu
1               5                   10

<210> SEQ ID NO 12
<211> LENGTH: 19
<212> TYPE: PRT
<213> ORGANISM: Pyrococcus furiosus

<400> SEQUENCE: 12

His Lys Ala Asp Ala Lys Tyr Pro Val Val Ser Ala Ala Ser Ile Leu
1               5                   10                  15

Ala Lys Val

<210> SEQ ID NO 13
<211> LENGTH: 16
<212> TYPE: PRT
<213> ORGANISM: Pyrococcus furiosus

<400> SEQUENCE: 13

Lys Leu Lys Lys Gln Tyr Gly Asp Phe Gly Ser Gly Tyr Pro Ser Asp
```

<210> SEQ ID NO 14
<211> LENGTH: 220
<212> TYPE: PRT
<213> ORGANISM: Pyrococcus horikoshii

<400> SEQUENCE: 14

| Met | Lys | Val | Ala | Gly | Val | Asp | Glu | Ala | Gly | Arg | Gly | Pro | Val | Ile | Gly |
|---|---|---|---|---|---|---|---|---|---|---|---|---|---|---|---|
| 1 | | | | 5 | | | | | 10 | | | | | 15 | |

| Pro | Leu | Val | Ile | Gly | Val | Ala | Val | Ile | Asp | Glu | Lys | Asn | Ile | Glu | Arg |
|---|---|---|---|---|---|---|---|---|---|---|---|---|---|---|---|
| | | | 20 | | | | | 25 | | | | | 30 | | |

| Leu | Arg | Asp | Ile | Gly | Val | Lys | Asp | Ser | Lys | Gln | Leu | Thr | Pro | Gly | Gln |
|---|---|---|---|---|---|---|---|---|---|---|---|---|---|---|---|
| | | 35 | | | | | 40 | | | | | 45 | | | |

| Arg | Glu | Lys | Leu | Phe | Ser | Lys | Leu | Ile | Asp | Ile | Leu | Asp | Asp | Tyr | Tyr |
|---|---|---|---|---|---|---|---|---|---|---|---|---|---|---|---|
| | 50 | | | | | 55 | | | | | 60 | | | | |

| Val | Leu | Val | Thr | Pro | Lys | Glu | Ile | Asp | Glu | Arg | His | His | Ser | Met |
|---|---|---|---|---|---|---|---|---|---|---|---|---|---|---|
| 65 | | | | 70 | | | | | 75 | | | | | 80 |

| Asn | Glu | Leu | Glu | Ala | Glu | Lys | Phe | Val | Val | Ala | Leu | Asn | Ser | Leu | Arg |
|---|---|---|---|---|---|---|---|---|---|---|---|---|---|---|---|
| | | | | 85 | | | | | 90 | | | | | 95 | |

| Ile | Lys | Pro | Gln | Lys | Ile | Tyr | Val | Asp | Ser | Ala | Asp | Val | Asp | Pro | Lys |
|---|---|---|---|---|---|---|---|---|---|---|---|---|---|---|---|
| | | | 100 | | | | | 105 | | | | | 110 | | |

| Arg | Phe | Ala | Ser | Leu | Ile | Lys | Ala | Gly | Leu | Lys | Tyr | Glu | Ala | Thr | Val |
|---|---|---|---|---|---|---|---|---|---|---|---|---|---|---|---|
| | | 115 | | | | | 120 | | | | | 125 | | | |

| Ile | Ala | Glu | His | Lys | Ala | Asp | Ala | Lys | Tyr | Glu | Ile | Val | Ser | Ala | Ala |
|---|---|---|---|---|---|---|---|---|---|---|---|---|---|---|---|
| | 130 | | | | | 135 | | | | | 140 | | | | |

| Ser | Ile | Ile | Ala | Lys | Val | Thr | Arg | Asp | Arg | Glu | Ile | Glu | Lys | Leu | Lys |
|---|---|---|---|---|---|---|---|---|---|---|---|---|---|---|---|
| 145 | | | | | 150 | | | | | 155 | | | | | 160 |

| Gln | Lys | Tyr | Gly | Glu | Phe | Gly | Ser | Gly | Tyr | Pro | Ser | Asp | Pro | Arg | Thr |
|---|---|---|---|---|---|---|---|---|---|---|---|---|---|---|---|
| | | | | 165 | | | | | 170 | | | | | 175 | |

| Lys | Glu | Trp | Leu | Glu | Glu | Tyr | Tyr | Lys | Gln | Tyr | Gly | Asp | Phe | Pro | Pro |
|---|---|---|---|---|---|---|---|---|---|---|---|---|---|---|---|
| | | | 180 | | | | | 185 | | | | | 190 | | |

| Ile | Val | Arg | Arg | Thr | Trp | Glu | Thr | Ala | Arg | Lys | Ile | Glu | Glu | Arg | Phe |
|---|---|---|---|---|---|---|---|---|---|---|---|---|---|---|---|
| | | 195 | | | | | 200 | | | | | 205 | | | |

| Arg | Lys | Asn | Gln | Leu | Thr | Leu | Asp | Lys | Phe | Leu | Lys |
|---|---|---|---|---|---|---|---|---|---|---|---|
| | 210 | | | | | 215 | | | | | 220 |

<210> SEQ ID NO 15
<211> LENGTH: 228
<212> TYPE: PRT
<213> ORGANISM: Thermococcus kodakarensis

<400> SEQUENCE: 15

| Met | Lys | Ile | Ala | Gly | Ile | Asp | Glu | Ala | Gly | Arg | Gly | Pro | Val | Ile | Gly |
|---|---|---|---|---|---|---|---|---|---|---|---|---|---|---|---|
| 1 | | | | 5 | | | | | 10 | | | | | 15 | |

| Pro | Met | Val | Ile | Ala | Ala | Val | Val | Asp | Glu | Asn | Ser | Leu | Pro | Lys |
|---|---|---|---|---|---|---|---|---|---|---|---|---|---|---|
| | | | 20 | | | | | 25 | | | | | 30 | |

| Leu | Glu | Glu | Leu | Lys | Val | Arg | Asp | Ser | Lys | Lys | Leu | Thr | Pro | Lys | Arg |
|---|---|---|---|---|---|---|---|---|---|---|---|---|---|---|---|
| | | 35 | | | | | 40 | | | | | 45 | | | |

| Arg | Glu | Lys | Leu | Phe | Asn | Glu | Ile | Leu | Gly | Val | Leu | Asp | Asp | Tyr | Val |
|---|---|---|---|---|---|---|---|---|---|---|---|---|---|---|---|
| | 50 | | | | | 55 | | | | | 60 | | | | |

| Ile | Leu | Glu | Leu | Pro | Pro | Asp | Val | Ile | Gly | Ser | Arg | Glu | Gly | Thr | Leu |
|---|---|---|---|---|---|---|---|---|---|---|---|---|---|---|---|
| 65 | | | | | 70 | | | | | 75 | | | | | 80 |

| Asn | Glu | Phe | Glu | Val | Glu | Asn | Phe | Ala | Lys | Ala | Leu | Asn | Ser | Leu | Lys |
|---|---|---|---|---|---|---|---|---|---|---|---|---|---|---|---|
| | | | | 85 | | | | | 90 | | | | | 95 | |

| Val | Lys | Pro | Asp | Val | Ile | Tyr | Ala | Asp | Ala | Ala | Asp | Val | Asp | Glu | Glu |

```
            100                 105                 110
Arg Phe Ala Arg Glu Leu Gly Glu Arg Leu Asn Phe Glu Ala Glu Val
            115                 120                 125

Val Ala Lys His Lys Ala Asp Asp Ile Phe Pro Val Val Ser Ala Ala
130                 135                 140

Ser Ile Leu Ala Lys Val Thr Arg Asp Arg Ala Val Glu Lys Leu Lys
145                 150                 155                 160

Glu Glu Tyr Gly Glu Ile Gly Ser Gly Tyr Pro Ser Asp Pro Arg Thr
                    165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
            195                 200                 205

Glu Ser Glu Lys Lys Ala Glu Arg Gln Ala Thr Leu Asp Arg Tyr
    210                 215                 220

Phe Arg Lys Val
225

<210> SEQ ID NO 16
<211> LENGTH: 211
<212> TYPE: PRT
<213> ORGANISM: Archaeoglobus profundus

<400> SEQUENCE: 16

Met Ile Ala Gly Ile Asp Glu Ala Gly Lys Gly Pro Val Ile Gly Pro
1               5                   10                  15

Leu Val Ile Cys Gly Val Leu Cys Asp Glu Glu Thr Val Glu Tyr Leu
            20                  25                  30

Lys Ser Val Gly Val Lys Asp Ser Lys Lys Leu Asp Arg Arg Lys Arg
        35                  40                  45

Glu Glu Leu Tyr Asn Ile Ile Lys Ser Leu Cys Lys Val Lys Val Leu
    50                  55                  60

Lys Ile Ser Val Glu Asp Leu Asn Arg Leu Met Glu Tyr Met Ser Ile
65                  70                  75                  80

Asn Glu Ile Leu Lys Arg Ala Tyr Val Glu Ile Ile Arg Ser Leu Met
                85                  90                  95

Pro Lys Val Val Tyr Ile Asp Cys Pro Asp Ile Asn Val Glu Arg Phe
            100                 105                 110

Lys His Glu Ile Glu Glu Arg Thr Gly Val Glu Val Phe Ala Ser His
        115                 120                 125

Lys Ala Asp Glu Ile Tyr Pro Ile Val Ser Ile Ala Ser Ile Val Ala
    130                 135                 140

Lys Val Glu Arg Asp Phe Glu Ile Asp Lys Leu Lys Lys Ile Tyr Gly
145                 150                 155                 160

Asp Phe Gly Ser Gly Tyr Pro Ser Asp Leu Arg Thr Ile Glu Phe Leu
                165                 170                 175

Arg Ser Tyr Leu Arg Glu His Lys Ser Phe Pro Pro Ile Val Arg Lys
            180                 185                 190

Arg Trp Lys Thr Leu Lys Arg Leu Thr Thr His Thr Leu Ser Asp Phe
            195                 200                 205

Phe Glu Val
    210

<210> SEQ ID NO 17
<211> LENGTH: 205
```

<212> TYPE: PRT
<213> ORGANISM: Archaeoglobus fulgidis

<400> SEQUENCE: 17

```
Met Lys Ala Gly Ile Asp Glu Ala Gly Lys Gly Cys Val Ile Gly Pro
1               5                   10                  15

Leu Val Ala Gly Val Ala Cys Ser Asp Glu Asp Arg Leu Arg Lys
            20                  25                  30

Leu Gly Val Lys Asp Ser Lys Lys Leu Ser Gln Gly Arg Arg Glu Glu
            35                  40                  45

Leu Ala Glu Glu Ile Arg Lys Ile Cys Arg Thr Glu Val Leu Lys Val
        50                  55                  60

Ser Pro Glu Asn Leu Asp Glu Arg Met Ala Ala Lys Thr Ile Asn Glu
65                  70                  75                  80

Ile Leu Lys Glu Cys Tyr Ala Glu Ile Ile Leu Arg Leu Lys Pro Glu
                85                  90                  95

Ile Ala Tyr Val Asp Ser Pro Asp Val Ile Pro Glu Arg Leu Ser Arg
            100                 105                 110

Glu Leu Glu Glu Ile Thr Gly Leu Arg Val Val Ala Glu His Lys Ala
        115                 120                 125

Asp Glu Lys Tyr Pro Leu Val Ala Ala Ala Ser Ile Ile Ala Lys Val
130                 135                 140

Glu Arg Glu Arg Glu Ile Glu Arg Leu Lys Glu Lys Phe Gly Asp Phe
145                 150                 155                 160

Gly Ser Gly Tyr Ala Ser Asp Pro Arg Thr Arg Glu Val Leu Lys Glu
                165                 170                 175

Trp Ile Ala Ser Gly Arg Ile Pro Ser Cys Val Arg Met Arg Trp Lys
            180                 185                 190

Thr Val Ser Asn Leu Arg Gln Lys Thr Leu Asp Asp Phe
            195                 200                 205
```

<210> SEQ ID NO 18
<211> LENGTH: 233
<212> TYPE: PRT
<213> ORGANISM: Thermococcus celer

<400> SEQUENCE: 18

```
Leu Lys Leu Ala Gly Ile Asp Glu Ala Gly Arg Gly Pro Val Ile Gly
1               5                   10                  15

Pro Met Val Ile Ala Ala Val Val Leu Asp Glu Lys Asn Val Pro Lys
            20                  25                  30

Leu Arg Asp Leu Gly Val Arg Asp Ser Lys Lys Leu Thr Pro Lys Arg
        35                  40                  45

Arg Glu Arg Leu Phe Asn Asp Ile Ile Lys Leu Leu Asp Asp Tyr Val
    50                  55                  60

Ile Leu Glu Leu Trp Pro Glu Glu Ile Asp Ser Arg Gly Gly Thr Leu
65                  70                  75                  80

Asn Glu Leu Glu Val Glu Arg Phe Val Glu Ala Leu Asn Ser Leu Lys
                85                  90                  95

Val Lys Pro Asp Val Val Tyr Ile Asp Ala Ala Asp Val Lys Glu Gly
            100                 105                 110

Arg Phe Gly Glu Glu Ile Lys Glu Arg Leu Asn Phe Glu Ala Lys Ile
        115                 120                 125

Val Ser Glu His Arg Ala Asp Asp Lys Phe Leu Pro Val Ser Ser Ala
    130                 135                 140
```

```
Ser Ile Leu Ala Lys Val Thr Arg Asp Arg Ala Ile Glu Lys Leu Lys
145                 150                 155                 160

Glu Lys Tyr Gly Glu Ile Gly Ser Gly Tyr Pro Ser Asp Pro Arg Thr
                165                 170                 175

Arg Glu Phe Leu Glu Asn Tyr Tyr Arg Gln His Gly Glu Phe Pro Pro
            180                 185                 190

Val Val Arg Arg Ser Trp Lys Thr Leu Arg Lys Ile Glu Glu Lys Leu
        195                 200                 205

Arg Lys Glu Ala Gly Ser Lys Asn Pro Glu Asn Ser Lys Glu Lys Gly
        210                 215                 220

Gln Thr Ser Leu Asp Val Phe Leu Arg
225                 230

<210> SEQ ID NO 19
<211> LENGTH: 224
<212> TYPE: PRT
<213> ORGANISM: Thermococcus litoralis

<400> SEQUENCE: 19

Met Lys Leu Gly Gly Ile Asp Glu Ala Gly Arg Gly Pro Val Ile Gly
1               5                   10                  15

Pro Leu Val Ile Ala Ala Val Val Asp Glu Ser Arg Met Gln Glu
                20                  25                  30

Leu Glu Ala Leu Gly Val Lys Asp Ser Lys Lys Leu Thr Pro Lys Arg
            35                  40                  45

Arg Glu Glu Leu Phe Glu Glu Ile Val Gln Ile Val Asp Asp His Val
        50                  55                  60

Ile Ile Gln Leu Ser Pro Glu Glu Ile Asp Gly Arg Asp Gly Thr Met
65                  70                  75                  80

Asn Glu Leu Glu Ile Glu Asn Phe Ala Lys Ala Leu Asn Ser Leu Lys
                85                  90                  95

Val Lys Pro Asp Val Leu Tyr Ile Asp Ala Ala Asp Val Lys Glu Lys
                100                 105                 110

Arg Phe Gly Asp Ile Ile Gly Glu Arg Leu Ser Phe Ser Pro Lys Ile
            115                 120                 125

Ile Ala Glu His Lys Ala Asp Ser Lys Tyr Ile Pro Val Ala Ala Ala
130                 135                 140

Ser Ile Leu Ala Lys Val Thr Arg Asp Arg Ala Ile Glu Lys Leu Lys
145                 150                 155                 160

Glu Leu Tyr Gly Glu Ile Gly Ser Gly Tyr Pro Ser Asp Pro Asn Thr
                165                 170                 175

Arg Arg Phe Leu Glu Glu Tyr Tyr Lys Ala His Gly Glu Phe Pro Pro
            180                 185                 190

Ile Val Arg Lys Ser Trp Lys Thr Leu Arg Lys Ile Glu Glu Lys Leu
        195                 200                 205

Lys Ala Lys Lys Thr Gln Pro Thr Ile Leu Asp Phe Leu Lys Lys Pro
        210                 215                 220
```

MODIFIED RNASE H AND DETECTION OF NUCLEIC ACID AMPLIFICATION

CROSS-REFERENCE TO RELATED APPLICATIONS

This application is a divisional application of U.S. patent application Ser. No. 13/108,311 filed on May 16, 2011 (now allowed), which claims priority from U.S. Provisional Patent Application No. 61/347,984, filed on May 25, 2010, the contents of which are hereby incorporated by reference in their entirety.

FIELD

The disclosure describes a modified RNAse H for improved real-time reverse transcriptase-PCR detection of RNA sequences.

BACKGROUND

One of the most widely used techniques to study gene expression exploits first-strand cDNA of mRNA sequence(s) as a template for PCR amplification. The ability to measure the kinetics of a PCR reaction in combination with reverse transcriptase-PCR techniques promises to facilitate the accurate and precise measurement of target RNA sequences with the requisite level of sensitivity. In particular, fluorescent dual-labeled hybridization probe technologies, such as the "CATACLEAVE™ endonuclease assay (described in detail in U.S. Pat. No. 5,763,181; see FIG. 1), permit the detection of reverse transcriptase-PCR amplification in real-time. Detection of target sequences is achieved by including a CATACLEAVE™ probe in the amplification reaction together with RNAse H. The CATACLEAVE™ probe, which is complementary to a target sequence within the reverse transcriptase-PCR amplification product, has a chimeric structure comprising an RNA sequence and a DNA sequence, and is flanked at its 5' and 3' ends by a detectable marker, for example FRET pair labeled DNA sequences. The proximity of the FRET pair's fluorescent label to the quencher precludes fluorescence of the intact probe. Upon annealing of the probe to the reverse transcriptase-PCR product a RNA: DNA duplex is generated that can be cleaved by RNAse H present in the reaction mixture. Cleavage within the RNA portion of the annealed probe results in the separation of the fluorescent label from the quencher and a subsequent emission of fluorescence.

SUMMARY

A reversibly modified 'hot start' RNAse H enzyme composition is described for improved CATACLEAVE™ probe detection of nucleic acid sequences in a test sample. A key feature of the enzyme composition is the ability to regulate the catalytic activity of the RNAse H during the course of a reverse transcription-PCR cycle. Thus, RNAse H activity can be initially suppressed to minimize degradation of RNA:DNA primer heteroduplexes prior to reverse transcription. After cDNA synthesis is complete, RNAse H activity is induced to promote the cleavage and fluorescent detection of CATACLEAVE™ probes that anneal to target DNA sequences within the reverse transcriptase-PCR products. The inducible RNAse H enzyme is amenable to high throughput applications requiring one step reverse transcriptase CATACLEAVE™ PCR in a single reaction mix.

In one embodiment, the invention includes a hot start enzyme composition comprising an enzyme having an inducible RNAse H activity. The enzyme may have a thermostable RNase H domain which can have at least 70%, 80% or 90%, 95% or 99% sequence identity to the amino acid sequence of SEQ ID NOs: 11, 12, 13 or 14.

The hot start composition can have a polymerase activity such as a DNA polymerase or reverse transcriptase activity. The RNAse H activity can be heat-inducible or pH inducible.

In one embodiment, the enzyme with the inducible RNAse H activity can be *Pyrococcus furiosus* RNase HII, *Pyrococcus horikoshi* RNase HII, *Thermococcus litoralis* RNase HI, *Thermus thermophilus* RNase HI, *E. coli* RNAse HI, or *E. coli* RNase HII.

The enzyme with an inducible RNAse H activity can be reversibly modified by a chemical modification. In an embodiment, the enzyme may be reversibly modified by acylation of an amino acid of the enzyme such as lysine or by reaction with formaldehyde having a concentration of about 0.2 to about 1% (w/v).

In one embodiment, the hot start enzyme composition further comprises a ligand, wherein the inducible RNAse H activity can be inhibited by the association of the enzyme with the ligand or induced by interference with the association of the enzyme with the ligand. The ligand can be thermolabile. The association between the enzyme and the ligand can be non-covalent.

The ligand can be a peptide, a nucleic acid or a small molecule having a $K_D$ dissociation constant of $10^{-1}$ M or less for the enzyme with the inducible RNAse H activity. In some embodiments, the ligand can bind to the RNAse H domain or it can induce a conformational change in the RNAse H domain.

The ligand can be an antibody, an antibody fragment, an aptamer, or a chelating agent.

The antibody fragment can be a Fab, a Fab', a $F(ab')_2$, a Fd, a single chain Fv or scFv, a disulfide linked Fv, a V-NAR domain, a IgNar, an intrabody, an $IgGDCH_2$, a minibody, a $F(ab')_3$, a tetrabody, a triabody, a diabody, a $(scFv)_2$, single-domain antibody, DVD-Ig, Fcab, $mAb_2$, or a scFv-Fc.

The RNAse H activity can be induced by (1) heating a solution containing the enzyme to a temperature of about 90° C. or higher or (2) by lowering the pH of a solution containing the enzyme to about 7.0 or lower. The solution can be a polymerase chain reaction sample comprising a target nucleic acid sequence.

The association between the enzyme and the ligand can be covalent. For example, the ligand can be a cross-linking agent.

In one embodiment, the invention discloses a method of amplifying a target sequence, having the steps of providing an amplification reaction mix having:
  a sample comprising a target DNA sequence;
  a hot start enzyme composition, comprising DNA polymerase and inducible RNAse H activities;
  a first primer comprising a sequence complementary to the 5' end of the target nucleic acid sequence;
  a second primer comprising a sequence complementary to the 3' end of the target nucleic acid sequence; and
  a probe which is coupled to a detectable label and having a composition capable of being cleaved by RNase H; and
  subjecting the amplification reaction composition to at least one amplification reaction to form at least one amplification product, and measuring the detectable label of the resulting amplification product, wherein the amplification reaction comprises a step of heating the reaction composition to a temperature of about 90° C.

The step of heating the reaction composition can be conducted at about 95° C.

The probe can be an oligonucleotide comprising one or more DNA sequence portions and a RNA sequence portion, wherein the RNA portion is disposed between two DNA sequences in a way that the 3' end and 5' end of the RNA sequence are coupled to each of the two DNA sequences.

The heating step can induce the RNAse H activity by disrupting the association between the enzyme with the RNAse H activity and the ligand. The ligand can be thermolabile.

In another embodiment the invention discloses a method for detecting a target ribonucleic acid sequence in a sample, having the steps of providing an amplification reaction composition comprising:
  a sample containing a target RNA sequence,
  a hot start enzyme composition comprising reverse transcriptase, DNA polymerase and inducible RNAse H activities wherein the RNAse H activity is inhibited by a ligand;
  a probe sequence which contains a detectable label and comprises a cleavage sequence of the RNase H;
  a first primer comprising a sequence complementary to the 5' end of the target nucleic acid sequence; and
  a second primer comprising a sequence complementary to the 3' end of the target nucleic acid sequence;
  initiating reverse transcription of the target RNA to form a RNA: (NOTE: cDNA implies that the product is double stranded DNA and not the reverse transcriptase product) DNA duplex;
  heating the reaction composition to a temperature of about 90° C. or higher thereby activating the inducible RNAse H activity to degrade the RNA moiety of the RNA: DNA duplex;
  initiating at least one amplification reaction to form at least one amplification product, and measuring the detectable label of the resulting amplification products.

The probe can be an oligonucleotide comprising one or more DNA sequence portions and a RNA sequence portion, wherein the RNA portion is disposed between two DNA sequences in a way that the 3' end and 5' end of the RNA sequence are coupled to each of the two DNA sequences. The target ribonucleic acid sequence can be a retrovirus. The step of heating the reaction composition can be conducted at about 95° C. The heating step may activate the inducible RNAse H activity. The ligand can be thermolabile.

In another embodiment, the invention describes a microarray having the hot start enzyme composition described herein.

In yet another embodiment, the invention discloses a method for detecting target ribonucleic acid sequences in a plurality of samples, having the steps of providing a microarray having a plurality of amplification reaction compositions each comprising:
  a sample containing a target RNA sequence,
  a hot start enzyme composition comprising reverse transcriptase, DNA polymerase and inducible RNAse H activities wherein the RNAse H activity is inhibited by a ligand;
  a probe sequence which contains a detectable label and comprises a cleavage sequence of the RNase H;
  a first primer comprising a sequence complementary to the 5' end of the target nucleic acid sequence; and
  a second primer comprising a sequence complementary to the 3' end of the target nucleic acid sequence;
  and for each amplification reaction composition in the microarray:
  initiating reverse transcription of the target RNA to form a RNA: cDNA duplex, heating the reaction composition to a temperature of about 90° C. or higher thereby activating the inducible RNAse H activity to degrade the RNA moiety of the RNA: cDNA duplex,
  initiating at least one amplification reaction to form at least one amplification product, and measuring the detectable label of the resulting amplification product.

The target ribonucleic acid sequence can be a retrovirus. The step of heating the reaction composition can be conducted at about 95° C. that can activate the inducible RNAse H activity. This ligand can be thermolabile.

In one embodiment, the invention discloses a kit having a microarray of hot start compositions that may include an enzyme with reverse transcriptase activity or DNA polymerase activity.

The previously described embodiments have many advantages, including using a modified RNAse H enzyme to improve the sensitivity of CATACLEAVE™ reverse transcription-PCR detection of RNA sequences. The improved detection method is fast, accurate and suitable for high throughput applications. Convenient, user-friendly and reliable diagnostic kits are also described for the high throughput detection of RNA sequences.

BRIEF DESCRIPTION OF THE DRAWINGS

The skilled artisan will understand that the drawings, described below, are for illustration purposes only. The figures are not intended to limit the scope of the teachings in any way.

DETAILED DESCRIPTION

Figure 1:
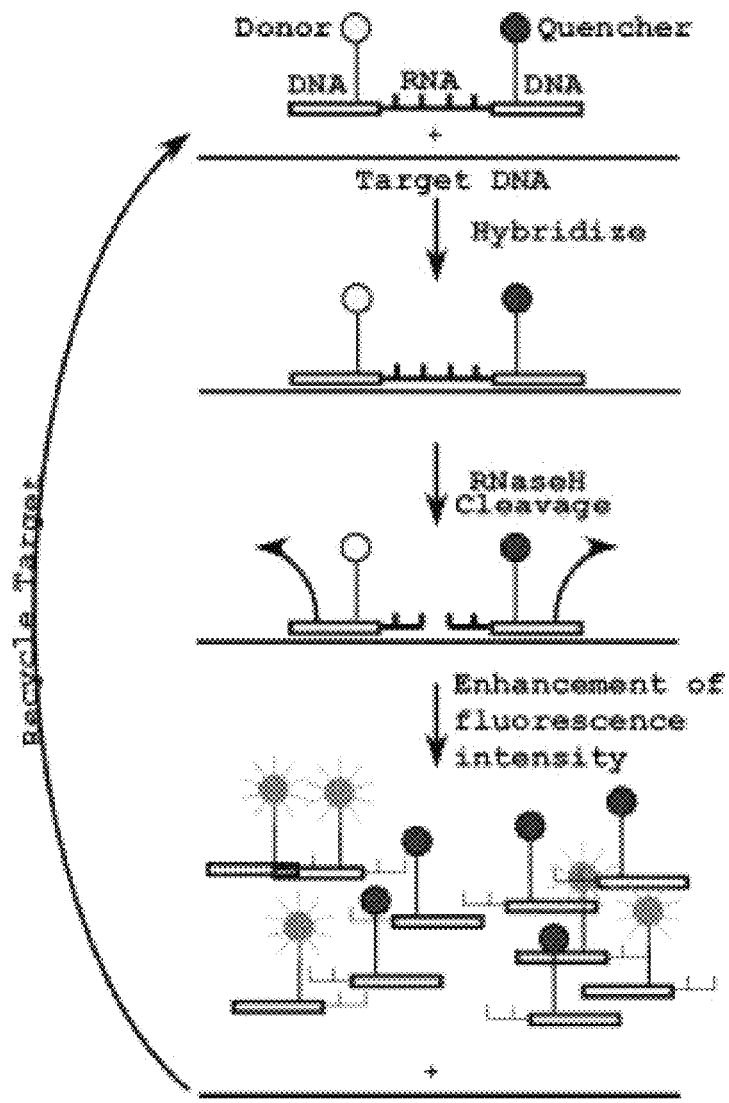
FIG. 1 is a schematic representation of CATACLEAVE™ probe technology, as described in U.S. Pat. No. 5,753,181.

The practice of the embodiments described herein employs, unless otherwise indicated, conventional molecular biological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements; Sambrook, et al., Molecular Cloning: A Laboratory Manual, 2nd Edition, Cold Spring Harbor, N.Y. (1989).

Unless defined otherwise, all technical and scientific terms used herein have the same meaning as is commonly understood by one of skill in the art. The specification also provides definitions of terms to help interpret the disclosure and claims of this application. In the event a definition is not consistent with definitions elsewhere, the definition set forth in this application will control.

RNAse H Enzymes and the RNAse H Domain

This application describes modified thermostable RNase H enzyme compositions for use in CataCleave™ reverse transcriptase PCR reactions.

RNase H hydrolyzes RNA in RNA-DNA hybrids. First identified in calf thymus, RNAse H has subsequently been described in a variety of organisms. Indeed, RNase H activity appears to be ubiquitous in eukaryotes and bacteria. Although RNase Hs form a family of proteins of varying molecular weight and nucleolytic activity, substrate requirements appear to be similar for the various isotypes. For example, most RNase Hs studied to date function as endonucleases and require divalent cations (e.g., $Mg^{2+}$, $Mn^2$) to produce cleavage products with 5' phosphate and 3' hydroxyl termini.

In prokaryotes, RNase H have been cloned and extensively characterized (see Crooke, et al., (1995) Biochem J, 312 (Pt 2), 599-608; Lima, et al., (1997) J Biol Chem, 272, 27513-27516; Lima, et al., (1997) Biochemistry, 36, 390-398; Lima, et al., (1997) J Biol Chem, 272, 18191-18199; Lima, et al., (2007) Mol Pharmacol, 71, 83-91; Lima, et al., (2007) Mol Pharmacol, 71, 73-82; Lima, et al., (2003) J Biol Chem, 278, 14906-14912; Lima, et al., (2003) J Biol Chem, 278, 49860-49867; Itaya, M., Proc. Natl. Acad. Sci. USA, 1990, 87, 8587-8591). For example, E. coli RNase HII is 213 amino acids in length whereas RNase HI is 155 amino acids long. E. coli RNase HII displays only 17% homology with E. coli RNase HI. An RNase H cloned from S. typhimurium differed from E. coli RNase HI in only 11 positions and was 155 amino acids in length (Itaya, M. and Kondo K., Nucleic Acids Res., 1991, 19, 4443-4449).

Proteins that display RNase H activity have also been cloned and purified from a number of viruses, other bacteria and yeast (Wintersberger, U. Pharmac. Ther., 1990, 48, 259-280). In many cases, proteins with RNase H activity appear to be fusion proteins in which RNase H is fused to the amino or carboxy end of another enzyme, often a DNA or RNA polymerase. The RNase H domain has been consistently found to be highly homologous to E. coli RNase HI, but because the other domains vary substantially, the molecular weights and other characteristics of the fusion proteins vary widely.

In higher eukaryotes two classes of RNase H have been defined based on differences in molecular weight, effects of divalent cations, sensitivity to sulfhydryl agents and immunological cross-reactivity (Busen et al., Eur. J. Biochem., 1977, 74, 203-208). RNase HI enzymes are reported to have molecular weights in the 68-90 kDa range, be activated by either $Mn^{2+}$ or $Mg^{2+}$ and be insensitive to sulfhydryl agents. In contrast, RNase H II enzymes have been reported to have molecular weights ranging from 31-45 kDa, to require $Mg^{2+}$ to be highly sensitive to sulfhydryl agents and to be inhibited by $Mn^{2+}$ (Busen, W., and Hausen, P., Eur. J. Biochem., 1975, 52, 179-190; Kane, C. M., Biochemistry, 1988, 27, 3187-3196; Busen, W., J. Biol. Chem., 1982, 257, 7106-7108)

A detailed comparison of RNAses from different species is reported in Ohtani N, Haruki M, Morikawa M, Kanaya S. J Biosci Bioeng. 1999; 88(1):12-9.

An enzyme with RNase HII characteristics has also been purified to near homogeneity from human placenta (Frank et al., Nucleic Acids Res., 1994, 22, 5247-5254). This protein has a molecular weight of approximately 33 kDa and is active in a pH range of 6.5-10, with a pH optimum of 8.5-9. The enzyme requires $Mg^{2+}$ and is inhibited by $Mn^{2+}$ and n-ethyl maleimide. The products of cleavage reactions have 3' hydroxyl and 5' phosphate termini.

Examples of RNase H enzymes, which may be employed in the embodiments, also include, but are not limited to, thermostable RNAse H enzymes isolated from thermophilic organisms such as *Pyrococcus furiosus* RNase HII, *Pyrococcus horikoshi* RNase HII, *Thermococcus litoralis* RNase HI, *Therms thermophilus* RNase HI. Other RNAse H enzymes that may be employed in the embodiments are described in, for example, U.S. Pat. No. 7,422,888 to Uemori or the published U.S. Patent Application No. 2009/0325169 to Walder, the contents of which are incorporated herein by reference.

In one embodiment, an RNAse H enzyme is a thermostable RNAse H with 40%, 50%, 60%, 70%, 80%, 90%, 95% or 99% homology with the amino acid sequence of Pfu RNase HII (SEQ ID NO: 1), shown below.

```
MKIGGIDEAG RGPAIGPLVV ATVVVDEKNI EKLRNIGVKD SKQLTPHERK NLFSQITSIA   60

DDYKIVIVSP EEIDNRSGTM NELEVEKFAL ALNSLQIKPA LIYADAADVD ANRFASLIER  120

RLNYKAKIIA EHKADAKYPV VSAASILAKV VRDEEIEKLK KQYGDFGSGY PSDPKTKKWL  180

EEYYKKHNSF PPIVRRTWET VRKIEESIKA KKSQLTLDKF FKKP                   224
```

The homology can be determined using, for example, a computer program DNASIS-Mac (Takara Shuzo), a computer algorithm FASTA (version 3.0; Pearson, W. R. et al., Pro. Natl. Acad. Sci., 85:2444-2448, 1988) or a computer algorithm BLAST (version 2.0, Altschul et al., Nucleic Acids Res. 25:3389-3402, 1997).

In another embodiment, an RNAse H enzyme is a thermostable RNAse H with at least one or more homology regions 1-4 corresponding to positions 5-20, 33-44, 132-150, and 158-173 of SEQ ID NO: 1

HOMOLOGY REGION 1: GIDEAG RGPAIGPLVV (SEQ ID NO: 10; corresponding to positions 5-20 of SEQ ID NO: 1)

HOMOLOGY REGION 2: LRNIGVKD SKQL (SEQ ID NO: 11; corresponding to positions 33-44 of SEQ ID NO: 1)

HOMOLOGY REGION 3: HKADAKYPV VSAASILAKV (SEQ ID NO: 12; corresponding to positions 132-150 of SEQ ID NO: 1)

HOMOLOGY REGION 4: KLK KQYGDFGSGY PSD (SEQ ID NO: 13; corresponding to positions 158-173 of SEQ ID NO: 1)

In another embodiment, an RNAse H enzyme is a thermostable RNAse H with at least one of the homology regions having 50%, 60%. 70%, 80%, 90% sequence identity with a polypeptide sequence of SEQ ID NOs: 10, 11, 12, or 13.

The terms "sequence identity" as used herein refers to the extent that sequences are identical or functionally or structurally similar on a amino acid to amino acid basis over a window of comparison. Thus, a "percentage of sequence identity", for example, can be calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

Modification of RNAse H

The term "modified RNase H," as used herein, can be an RNase H reversely coupled to or reversely bound to an inhibiting factor that causes the loss of the endonuclease activity of the RNase H. Release or decoupling of the inhibiting factor from the RNase H restores at least partial or full activity of the endonuclease activity of the RNase H. About 30-100% of its activity of an intact RNase H may be sufficient. The inhibiting factor may be a ligand or a chemical modification. The ligand can be an antibody, an aptamer, a receptor, a cofactor, or a chelating agent. The ligand can bind to the active site of the RNAse H enzyme thereby inhibiting enzymatic activity or it can bind to a site remote from the RNAse's active site. In some embodiment, the ligand may induce a conformational change. The chemical modification can be a crosslinking (for example, by formaldehyde) or acylation. The release or decoupling of the inhibiting factor from the RNase HII may be accomplished by heating a sample or a mixture containing the coupled RNase HII (inactive) to a temperature of about 65° C. to about 95° C. or higher, and/or lowering the pH of the mixture or sample to about 7.0 or lower.

The term "inactivated RNase H" or "inactive RNase H," as used herein, refers to an RNase H, which lost its endonuclease activity by more than about 75% or by more than about 85% or by more than about 95% as compared to unmodified RNase H (considered as 100%) determined at 50° C. under otherwise identical experimental conditions.

The term "activated RNase H" or "active RNase H," as used herein, refers to an RNase HII, which has been modified as described above, recovers its endonuclease activity by more than about 5% or about 10% or about 15% or about 20% or about 25% or about 30% or more as compared to unmodified RNase H (considered as 100%) determined at 50° C. under otherwise identical experimental conditions.

As used herein, an "inducible" RNAse H activity refers to the herein described modified RNAse H that has an endonuclease catalytic activity that can be regulated by association with a ligand. Under permissive conditions, the RNAse H endonuclease catalytic activity is activated whereas at non-permissive conditions, this catalytic activity is inhibited. In some embodiments, the catalytic activity of a modified RNAse H can be inhibited at temperature conducive for reverse transcription, i.e. about 42° C., and activated at more elevated temperatures found in PCR reactions, i.e. about 65° C. to 95° C. A modified RNAse H with these characteristics is said to be "heat inducible."

In other embodiments, the catalytic activity of a modified RNAse H can be regulated by changing the pH of a solution containing the enzyme.

As used herein, a "hot start" enzyme composition refers to compositions having an enzymatic activity that is inhibited at non-permissive temperatures, i.e. from about 25° C. to about 45° C. and activated at temperatures compatible with a PCR reaction, e.g. about 55° C. to about 95° C. In certain embodiment, a "hot start" enzyme composition may have a 'hot start' RNAse H and/or a 'hot start' thermostable DNA polymerase that are known in the art.

Crosslinking of RNAse H enzymes can be performed using, for example, formaldehyde. In one embodiment, a thermostable RNase HII is subjected to controlled and limited crosslinking using formaldehyde. By heating an amplification reaction composition, which comprises the modified RNase HII in an inactive state, to a temperature of about 95° C. or higher for an extended time, for example about 15 minutes, the crosslinking is reversed and the RNase HII activity is restored.

In general, the lower the degree of crosslinking, the higher the endonuclease activity of the enzyme is after reversal of crosslinking. The degree of crosslinking may be controlled by varying the concentration of formaldehyde and the duration of crosslinking reaction. For example, about 0.2% (w/v), about 0.4% (w/v), about 0.6% (w/v), or about 0.8% (w/v) of formaldehyde may be used to crosslink an RNase H enzyme. About 10 minutes of crosslinking reaction using 0.6% formaldehyde may be sufficient to inactivate RNase HII from *Pyrococcus furiosus*.

The crosslinked RNase HII does not show any measurable endonuclease activity at about 37° C. In some cases, a measurable partial reactivation of the crosslinked RNase HII may occur at a temperature of around 50° C., which is lower than the PCR denaturation temperature. To avoid such unintended reactivation of the enzyme, it may be required to store or keep the modified RNase HII at a temperature lower than 50° C. until its reactivation.

In general, PCR requires heating the amplification composition at each cycle to about 95° C. to denature the double stranded target sequence which will also release the inactivating factor from the RNase H, partially or fully restoring the activity of the enzyme.

RNase H may also be modified by subjecting the enzyme to acylation of lysine residues using an acylating agent, for example, a dicarboxylic acid. Acylation of RNase H may be performed by adding cis-aconitic anhydride to a solution of RNase H in an acylation buffer and incubating the resulting mixture at about 1-20° C. for 5-30 hours. In one embodiment, the acylation may be conducted at around 3-8° C. for 18-24 hours. The type of the acylation buffer is not particularly limited. In an embodiment, the acylation buffer has a pH of between about 7.5 to about 9.0.

The activity of acylated RNase H can be restored by lowering the pH of the amplification composition to about 7.0 or less. For example, when Tris buffer is used as a buffering agent, the composition may be heated to about 95° C., resulting in the lowering of pH from about 8.7 (at 25° C.) to about 6.5 (at 95° C.).

The duration of the heating step in the amplification reaction composition may vary depending on the modified RNase H, the buffer used in the PCR, and the like. However, in general, heating the amplification composition to 95° C. for about 30 seconds-4 minutes is sufficient to restore RNase H activity. In one embodiment, using a commercially available buffer such as Invitrogen AgPath™ buffer, full activity of *Pyrococcus furiosus* RNase HII is restored after about 2 minutes of heating.

RNase H activity may be determined using methods that are well known in the art. For example, according to a first method, the unit activity is defined in terms of the acid-solubilization of a certain number of moles of radiolabeled polyadenylic acid in the presence of equimolar polythymidylic acid under defined assay conditions (see Epicentre Hybridase thermostable RNase HI). In the second method, unit activity is defined in terms of a specific increase in the relative fluorescence intensity of a reaction containing equimolar amounts of the probe and a complementary template DNA under defined assay conditions. This second method is explained in more detail in the working Examples.

Methods of using a modified RNAse H according to the invention are hereby disclosed in the context of an exemplary embodiment of detecting an RNA sequence in a test sample using Catacleave™ reverse transcriptase PCR detection.

Nucleic Acid Template Preparation

In some embodiments, the sample comprises a purified nucleic acid template (e.g., mRNA, rRNA, and mixtures thereof). Procedures for the extraction and purification of RNA from samples are well known in the art. For example, RNA can be isolated from cells using the TRIzol™ reagent (Invitrogen) extraction method. RNA quantity and quality is then determined using, for example, a Nanodrop™ spectrophotometer and an Agilent 2100 bioanalyzer.

In other embodiments, the sample is a cell lysate that is produced by lysing cells using a lysis buffer having a pH of about 6 to about 9, a zwitterionic detergent at a concentration of about 0.125% to about 2%, an azide at a concentration of about 0.3 to about 2.5 mg/ml and a protease such as proteinase K (about 1 mg/ml). After incubation at 55° C. for 15 minutes, the proteinase K is inactivated at 95° C. for 10 minutes to produce a "substantially protein free" lysate that is compatible with high efficiency PCR or reverse transcription PCR analysis.

In one embodiment, the 1× lysis reagent contains 12.5 mM Tris acetate or Tris-HCl or HEPES (4-(2-hydroxyethyl)-1-piperazineethanesulfonic acid) (pH=7-8), 0.25% (w/v) CHAPS, 0.3125 mg/ml sodium azide and proteinase K at 1 mg/ml.

The term "lysate" as used herein, refers to a liquid phase with lysed cell debris and nucleic acids.

As used herein, the term "substantially protein free" refers to a lysate where most proteins are inactivated by proteolytic cleavage by a protease. Protease may include proteinase K. Addition of proteinase K during cell lysis rapidly inactivates nucleases that might otherwise degrade the target nucleic acids. The "substantially protein free" lysate may be or may not be subjected to a treatment to remove inactivated proteins.

As used herein, the term "cells" can refer to prokaryotic or eukaryotic cells.

In one embodiment, the term "cells" can refer to microorganisms such as bacteria including, but not limited to gram positive bacteria, gram negative bacteria, acid-fast bacteria and the like. In certain embodiments, the "cells" to be tested may be collected using swab sampling of surfaces. In other embodiments, the "cells" can refer to pathogenic organisms.

In other embodiments, the sample comprises a viral nucleic acid, for example, a retroviral nucleic acid. In certain embodiment, a sample may contain a lentiviral nucleic acid such as HIV-1 or HIV-2.

As used herein, "zwitterionic detergent" refers to detergents exhibiting zwitterionic character (e.g., does not possess a net charge, lacks conductivity and electrophoretic mobility, does not bind ion-exchange resins, breaks protein-protein interactions), including, but not limited to, CHAPS, CHAPSO and betaine derivatives, e.g. preferably sulfobetaines sold under the brand names Zwittergent® (Calbiochem, San Diego, Calif.) and Anzergent® (Anatrace, Inc. Maumee, Ohio).

In one embodiment, the zwitterionic detergent is CHAPS (CAS Number: 75621-03-3; available from SIGMA-ALDRICH product no. C3023-1G), an abbreviation for 3-[(3-cholamidopropyl)dimethylammonio]-1-propanesulfonate (described in further detail in U.S. Pat. No. 4,372,888) having the structure:

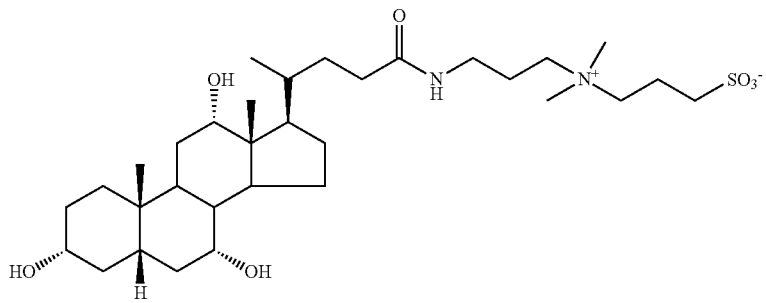

In a further embodiment, CHAPS is present at a concentration of about 0.125% to about 2% weight/volume (w/v) of the total composition. In a further embodiment, CHAPS is present at a concentration of about 0.25% to about 1% w/v of the total composition. In yet another embodiment, CHAPS is present at a concentration of about 0.4% to about 0.7% w/v of the total composition.

In other embodiments, the lysis buffer may include other non-ionic detergents such as Nonidet, Tween or Triton X-100.

As used herein, the term "buffer" refers to a composition that can effectively maintain the pH value between 6 and 9, with a $pK_a$ at 25° C. of about 6 to about 9. The buffer described herein is generally a physiologically compatible buffer that is compatible with the function of enzyme activities and enables biological macromolecules to retain their normal physiological and biochemical functions.

Examples of buffers include, but are not limited to, HEPES ((4-(2-hydroxyethyl)-1-piperazineethanesulfonic acid), MOPS (3-(N-morpholino)-propanesulfonic acid), N-tris(hydroxymethyl)methylglycine acid (Tricine), tris(hydroxymethyl)methylamine acid (Tris), piperazine-N,N'-bis (2-ethanesulfonic acid) (PIPES) and acetate or phosphate containing buffers ($K_2HPO_4$, $KH_2PO_4$, $Na_2HPO_4$, $NaH_2PO_4$) and the like.

The term "azide" as used herein is represented by the formula $—N_3$. In one embodiment, the azide is sodium azide $NaN_3$ (CAS number 26628-22-8; available from SIGMA-ALDRICH Product number: S2002-25G) that acts as a general bacterioside.

The term "protease," as used herein, is an enzyme that hydrolyses peptide bonds (has protease activity). Proteases are also called, e.g., peptidases, proteinases, peptide hydrolases, or proteolytic enzymes. The proteases for use according to the invention can be of the endo-type that act internally in polypeptide chains (endopeptidases). In one embodiment, the protease can be the serine protease, proteinase K (EC 3.4.21.64; available from Roche Applied Sciences, recombinant proteinase K 50 U/ml (from *Pichia pastoris*) Cat. No. 03 115 887 001).

Proteinase K is used to digest protein and remove contamination from preparations of nucleic acid. Addition of proteinase K to nucleic acid preparations rapidly inactivates nucleases that might otherwise degrade the DNA or RNA during purification. It is highly-suited to this application since the enzyme is active in the presence of chemicals that denature proteins and it can be inactivated at temperatures of about 95° C. for about 10 minutes.

In one embodiment, lysis of gram positive and gram negative bacteria, such as *Listeria, Salmonella*, and *E. Coli* also requires the lysis reagent include proteinase K (1 mg/ml). Protein in the cell lysate is digested by proteinase K for 15 minutes at 55° C. followed by inactivation of the proteinase K at 95° C. for 10 minutes. After cooling, the substantially protein free lysate is compatible with high efficiency PCR amplification.

In addition to or in lieu of proteinase K, the lysis reagent can comprise a serine protease such as trypsin, chymotrypsin, elastase, subtilisin, streptogrisin, thermitase, aqualysin, plasmin, cucumisin, or carboxypeptidase A, D, C, or Y. In addition to a serine protease, the lysis solution can comprise a cysteine protease such as papain, calpain, or clostripain; an acid protease such as pepsin, chymosin, or cathepsin; or a metalloprotease such as pronase, thermolysin, collagenase, dispase, an aminopeptidase or carboxypeptidase A, B, E/H, M, T, or U. Proteinase K is stable over a wide pH range (pH 4.0-10.0) and is stable in buffers with zwitterionic detergents.

Reverse Transcriptase-PCR Amplification

The reverse transcriptase-PCR procedure can be set up as either an end-point or real-time assay. cDNA amplification requires essentially two separate molecular syntheses: (i) the synthesis of cDNA from an RNA template; and (ii) the replication of the newly synthesized cDNA through PCR amplification. To attempt to address the technical problems often associated with reverse transcriptase-PCR, a number of protocols have been developed taking into account the three basic steps of the procedure: (a) the denaturation of RNA and the hybridization of reverse primer; (b) the synthesis of cDNA; and (c) PCR amplification. In the so called "uncoupled" reverse transcriptase-PCR procedure (e.g., two step reverse transcriptase-PCR), reverse transcription is performed as an independent step using the optimal buffer condition for reverse transcriptase activity. Following cDNA synthesis, the reaction is diluted to decrease $MgCl_2$, and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" reverse transcriptase PCR methods use a common buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{2+}$ then PCR is carried out in the presence of $Mg^{2+}$ after the removal of $Mn^{2+}$ by a chelating agent. Finally, the "continuous" method (e.g., one step reverse transcriptase-PCR) integrates the three reverse transcriptase-PCR steps into a single continuous reaction that avoids the opening of the reaction tube for component or enzyme addition. Continuous reverse transcriptase-PCR has been described as a single enzyme system using the reverse transcriptase activity of thermostable Taq DNA Polymerase and Tth polymerase and as a two enzyme system using AMV reverse transcriptase and Taq DNA Polymerase wherein the initial 65° C. RNA denaturation step is omitted.

To maintain the highest sensitivity it is important that the RNA not be degraded prior to cDNA synthesis. As noted above, the presence of RNase H in one step reverse transcription PCR protocols can cause unwanted degradation of the RNA:DNA primer hybrid before it can serve as a substrate for reverse transcriptase. The modified RNase H described herein resolves this issue by inactivating RNAse H endonuclease catalytic activity at temperatures required for reverse transcription, i.e. about 45-55° C. For example, a hot start RNAse H activity, as used herein, can be an RNAse H with a reversible chemical modification produced after reaction of the RNAse H with cis-aconitic anhydride under alkaline conditions. When the modified enzyme is used in a reaction with a Tris based buffer and the temperature is raised to 95° C. the pH of the solution drops and RNase H activity is restored. This method allows for the inclusion of RNase H in the reaction mixture prior to the initiation of reverse transcription.

The first step in real-time, reverse-transcription PCR is to generate the complementary DNA strand using one of the template specific DNA primers. In traditional PCR reactions this product is denatured, the second template specific primer binds to the cDNA, and is extended to form duplex DNA. This product is then amplified in subsequent rounds of PCR amplification.

The term "polymerase chain reaction" (PCR) refers to a method for amplification well known in the art for increasing the concentration of a segment of a target polynucleotide in a sample, where the sample can be a single polynucleotide species, or multiple polynucleotides. Generally, the PCR process consists of introducing a molar excess of two or more extendable oligonucleotide primers to a 10-100 µl reaction mixture comprising a sample, a buffering agent, a thermostable DNA polymerase, target nucleic acid sequence(s), dNTPs (each of the four deoxynucleotides dATP, dCTP, dGTP, and dTTP), and primers that are complementary to opposite strands of the double stranded target sequence in the sample. The reaction mixture is subjected to a program of thermal cycling in the presence of a DNA polymerase, resulting in the amplification of the desired target sequence flanked by the DNA primers. One PCR reaction may consist of about 5 to about 100 "cycles" of denaturation and synthesis of a polynucleotide molecule.

The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226; and U.S. Pat. Nos. 6,268,490 and 6,794,499).

As used herein, the term "nucleic acid" refers to an oligonucleotide or polynucleotide, wherein said oligonucleotide or polynucleotide may be modified or may comprise modified bases. Oligonucleotides are single-stranded polymers of nucleotides comprising from 2 to 60 nucleotides. Polynucleotides are polymers of nucleotides comprising two or more nucleotides. Polynucleotides may be either double-stranded DNAs, including annealed oligonucleotides wherein the second strand is an oligonucleotide with the reverse complement sequence of the first oligonucleotide, single-stranded nucleic acid polymers comprising deoxythymidine, single-stranded RNAs, double stranded RNAs or RNA/DNA heteroduplexes. Nucleic acids include, but are not limited to, genomic DNA, RNA, cDNA, hnRNA, snRNA, mRNA, rRNA, tRNA, miRNA, siRNA, fragmented nucleic acid, nucleic acid obtained from subcellular organelles such as mitochondria or chloroplasts, and nucleic acid obtained from microorganisms or DNA or RNA viruses that may be present on or in a biological sample. Nucleic acids may be composed of a single type of sugar moiety, e.g., as in the case of RNA and DNA, or mixtures of different sugar moieties, e.g., as in the case of RNA/DNA chimeras. In the specification, the nucleotides "A," "C," and "G" may be either a deoxyribonucleotide or ribonucleotide, and ribonucleotide A, ribonucleotide C, and ribonucleotide G are indicated by "rA," "rC," and "rG," respectively in the sequences of oligonucleotides.

A "target DNA" or "target RNA"" or "target nucleic acid," or "target nucleic acid sequence" refers to a nucleic acid that is targeted for DNA amplification. A target nucleic acid sequence serves as a template for amplification in a PCR reaction or reverse transcriptase-PCR reaction. Target nucleic acid sequences may include both naturally occurring and synthetic molecules. Exemplary target nucleic acid sequences include, but are not limited to, genomic DNA or genomic RNA.

As used herein, the term "oligonucleotide" is used sometimes interchangeably with "primer" or "polynucleotide." The term "primer" refers to an oligonucleotide that acts as a point of initiation of DNA synthesis in a PCR reaction. A primer is usually about 15 to about 35 nucleotides in length and hybridizes to a region complementary to the target sequence.

Oligonucleotides may be synthesized and prepared by any suitable methods (such as chemical synthesis), which are known in the art. Oligonucleotides may also be conveniently available through commercial sources.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

A "buffering agent" or "buffer" is a compound added to an amplification reaction which modifies the stability, activity, and/or longevity of one or more components of the amplification reaction by regulating the pH of the amplification reaction. Certain buffering agents are well known in the art and include, but are not limited to, Tris, Tricine, MOPS (3-(N-morpholino)propanesulfonic acid), and HEPES (4-(2-hydroxyethyl)-1-piperazineethanesulfonic acid).

The term "sample" refers to any substance containing nucleic acid material.

An additive is a compound added to a composition which modifies the stability, activity, and/or longevity of one or more components of the composition. In certain embodiments, the composition is an amplification reaction composition. In certain embodiments, an additive inactivates contaminant enzymes, stabilizes protein folding, and/or decreases aggregation. Exemplary additives that may be included in an amplification reaction include, but are not limited to, betaine, formamide, KCl, CaCl2, MgOAc, MgCl2, NaCl, NH4OAc, NaI, Na(CO3)2, LiCl, MnOAc, NMP, trehalose, demethylsulfoxide ("DMSO"), glycerol, ethylene glycol, dithiothreitol ("DTT"), pyrophosphatase (including, but not limited to Thermoplasma acidophilum inorganic pyrophosphatase ("TAP")), bovine serum albumin ("BSA"), propylene glycol, glycinamide, CHES, Percoll™, aurintricarboxylic acid, Tween 20, Tween 21, Tween 40, Tween 60, Tween 85, Brij 30, NP-40, Triton X-100, CHAPS, CHAPSO, Mackernium, LDAO (N-dodecyl-N,N-dimethylamine-N-oxide), Zwittergent 3-10, Xwittergent 3-14, Xwittergent SB 3-16, Empigen, NDSB-20, T4G32, E. Coli SSB, RecA, nicking endonucleases, 7-deazaG, dUTP, and UNG, anionic detergents, cationic detergents, non-ionic detergents, zwittergent, sterol, osmolytes, cations, and any other chemical, protein, or cofactor that may alter the efficiency of amplification. In certain embodiments, two or more additives are included in an amplification reaction.

As used herein, "DNA polymerase activity" refers to an enzymatic activity that catalyzes the polymerization of deoxyribonucleotides. Generally, the enzyme will initiate synthesis at the 3'-end of the primer annealed to a nucleic acid template sequence, and will proceed toward the 5' end of the template strand. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475: 32), *Thermococcus litoralis* (Tli) DNA polymerase (also referred to as Vent DNA polymerase, Cariello et al., 1991, Nucleic Acids Res, 19: 4193), 9° Nm DNA polymerase (discontinued product from New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus* kodakaraensis KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzymes can be determined by means well known in the art. One unit of DNA polymerase activity, according to the subject invention, is defined as the amount of enzyme which catalyzes the incorporation of 10 nmoles of total dNTPs into polymeric form in 30 minutes at optimal temperature (e.g., 72° C. for Pfu DNA polymerase).

The term "reverse transcriptase activity" and "reverse transcription" refers to the enzymatic activity of a class of polymerases characterized as RNA-dependent DNA polymerases that can synthesize a DNA strand (i.e., complementary DNA, cDNA) utilizing an RNA strand as a template.

"Reverse transcriptase-PCR" is a PCR reaction that uses RNA template and a reverse transcriptase, or an enzyme having reverse transcriptase activity, to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction.

Exemplary reverse transcriptases include, but are not limited to, the Moloney murine leukemia virus (M-MLV) RT as described in U.S. Pat. No. 4,943,531, a mutant form of M-MLV-RT lacking RNase H activity as described in U.S. Pat. No. 5,405,776, bovine leukemia virus (BLV) RT, Rous sarcoma virus (RSV) RT, Avian Myeloblastosis Virus (AMV) RT and reverse transcriptases disclosed in U.S. Pat. No. 7,883,871.

For PCR amplifications, the enzymes used in the invention are preferably thermostable. The term "thermostable" refers to an enzyme which is stable to heat, is heat resistant, and functions at high temperatures, e.g., 50° C. to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from about 85° C., for shorter polynucleotides, to about 105° C. for a time depending mainly on the temperature and the polynucleotide length, typically from about 0.25 minutes for shorter polynucleotides, to about 4.0 minutes for longer pieces of DNA. Higher temperatures may be tolerated as the buffer salt concentration and/or GC composition of the polynucleotide is increased. Preferably, the enzyme will not become irreversibly denatured at about 90° C. to about 100° C. An enzyme that does not become irreversibly denatured, according to the invention, retains at least about 10%, or at least about 25%, or at least about 50% or more function or activity during the amplification reaction.

In certain embodiments, one or more primers may be labeled. As used herein, "label," "detectable label," or "marker," or "detectable marker," which are interchangeably used in the specification, refers to any chemical moiety attached to a nucleotide, nucleotide polymer, or nucleic acid binding factor, wherein the attachment may be covalent or non-covalent. Preferably, the label is detectable and renders the nucleotide or nucleotide polymer detectable to the practitioner of the invention. Detectable labels include luminescent molecules, chemiluminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

One step reverse transcriptase-PCR provides several advantages over uncoupled reverse transcriptase-PCR. One step reverse transcriptase-PCR requires less handling of the reaction mixture reagents and nucleic acid products than uncoupled reverse transcriptase-PCR (e.g., opening of the reaction tube for component or enzyme addition in between the two reaction steps), and is therefore less labor intensive, reducing the required number of person hours. One step reverse transcriptase-PCR also requires less sample, and reduces the risk of contamination. The sensitivity and specificity of one-step reverse transcriptase-PCR has proven well suited for studying expression levels of one to several genes in a given sample or the detection of pathogen RNA. Typically, this procedure has been limited to the use of gene-specific primers to initiate cDNA synthesis.

The ability to measure the kinetics of a PCR reaction by real-time detection in combination with these reverse transcriptase-PCR techniques has enabled accurate and precise determination of RNA copy number with high sensitivity. This has become possible by detecting the reverse transcriptase-PCR product through fluorescence monitoring and measurement of PCR product during the amplification process by fluorescent dual-labeled hybridization probe technologies, such as the 5' fluorogenic nuclease assay ("TaqMan") or endonuclease assay ("CataCleave"), discussed below.

Real-Time PCR of a *Salmonella* Target Nucleic Acid Sequence Using a CataCleave Probe Post-amplification amplicon detection is both laborious and time consuming. Real-time methods have been developed to monitor amplification during the PCR process. These methods typically employ fluorescently labeled probes that bind to the newly synthesized DNA or dyes whose fluorescence emission is increased when intercalated into double stranded DNA.

The probes are generally designed so that donor emission is quenched in the absence of target by fluorescence resonance energy transfer (FRET) between two chromophores. The donor chromophore, in its excited state, may transfer energy to an acceptor chromophore when the pair is in close proximity. This transfer is always non-radiative and occurs through dipole-dipole coupling. Any process that sufficiently increases the distance between the chromophores will decrease FRET efficiency such that the donor chromophore emission can be detected radiatively. Common donor chromophores include FAM, TAMRA, VIC, JOE, Cy3, Cy5, and Texas Red. Acceptor chromophores are chosen so that their excitation spectra overlap with the emission spectrum of the donor. An example of such a pair is FAM-TAMRA. There are also non fluorescent acceptors that will quench a wide range of donors. Other examples of appropriate donor-acceptor FRET pairs will be known to those skilled in the art.

Common examples of FRET probes that can be used for real-time detection of PCR include molecular beacons (e.g., U.S. Pat. No. 5,925,517 TaqMan probes (e.g., U.S. Pat. Nos. 5,210,015 and 5,487,972), and CataCleave probes (e.g., U.S. Pat. No. 5,763,181). The molecular beacon is a single stranded oligonucleotide designed so that in the unbound state the probe forms a secondary structure where the donor and acceptor chromophores are in close proximity and donor emission is reduced. At the proper reaction temperature the beacon unfolds and specifically binds to the amplicon. Once unfolded the distance between the donor and acceptor chromophores increases such that FRET is reversed and donor emission can be monitored using specialized instrumentation. TaqMan and CataCleave technologies differ from the molecular beacon in that the FRET probes employed are cleaved such that the donor and acceptor chromophores become sufficiently separated to reverse FRET.

TaqMan technology employs a single stranded oligonucleotide probe that is labeled at the 5' end with a donor chromophore and at the 3' end with an acceptor chromophore. The DNA polymerase used for amplification must contain a 5'->3' exonuclease activity. The TaqMan probe binds to one strand of the amplicon at the same time that the primer binds. As the DNA polymerase extends the primer the polymerase will eventually encounter the bound TaqMan probe. At this time the exonuclease activity of the polymerase will sequentially degrade the TaqMan probe starting at the 5' end. As the probe is digested the mononucleotides comprising the probe are released into the reaction buffer. The donor diffuses away from the acceptor and FRET is reversed. Emission from the donor is monitored to identify probe cleavage. Because of the way TaqMan works a specific amplicon can be detected only once for every cycle of PCR. Extension of the primer through the TaqMan target site generates a double stranded product that prevents further binding of TaqMan probes until the amplicon is denatured in the next PCR cycle.

U.S. Pat. No. 5,763,181, the content of which is incorporated herein by reference, describes another real-time detection method (referred to as "CataCleave" herein). CataCleave technology differs from TaqMan in that cleavage of the probe is accomplished by a second enzyme that does not have polymerase activity. The CataCleave probe has a sequence within the molecule which is a target of an endonuclease, such as, for example a restriction enzyme or RNAase. In one example, the CataCleave probe has a chimeric structure where the 5' and 3' ends of the probe are constructed of DNA and the cleavage site contains RNA. The DNA sequence portions of the probe are labeled with a FRET pair either at the ends or internally. The PCR reaction includes an RNase H enzyme that will specifically cleave the RNA sequence portion of a RNA-DNA duplex (see FIG. 2). After cleavage, the two halves of the probe dissociate from the target amplicon at the reaction temperature and diffuse into the reaction buffer. As the donor and acceptors separate FRET is reversed in the same way as the TaqMan probe and donor emission can be monitored. Cleavage and dissociation regenerates a site for further CataCleave binding. In this way it is possible for a single amplicon to serve as a target or multiple rounds of probe cleavage until the primer is extended through the CataCleave probe binding site.

Labeling of a CataCleave Probe

The term "probe" comprises a polynucleotide having a specific portion designed to hybridize in a sequence-specific manner with a complementary region of a specific nucleic acid sequence, e.g., a target nucleic acid sequence. In one embodiment, the oligonucleotide probe is in the range of about 15 to about 60 nucleotides in length. In another embodiments, the oligonucleotide probe is in the range of about 18 to about 30 nucleotides in length. The precise sequence and length of an oligonucleotide probe depends in part on the nature of the target polynucleotide to which it binds. The binding location and length may be varied to achieve appropriate annealing and melting properties for a particular embodiment. Guidance for making such design choices can be found in many of the references describing Taq-man assays or CataCleave, described in U.S. Pat. Nos. 5,763,181, 6,787,304, and 7,112,422, the contents of which contents are incorporated herein by reference in their entirety.

The probe may be labeled with a "label" or "detectable label" as discussed above. In an embodiment, the label is a fluorochrome compound that is attached to the probe by covalent or non-covalent means.

As used herein, "fluorochrome" refers to a fluorescent compound that emits light upon excitation by light of a shorter wavelength than the light that is emitted. The term "fluorescent donor" or "fluorescence donor" refers to a fluorochrome that emits light that is measured in the assays described in the present invention. More specifically, a fluorescent donor provides energy (The transfer is non radiative, that is why I removed the word "light" that is absorbed by a fluorescence acceptor. The term "fluorescent acceptor" or "fluorescence acceptor" refers to either a second fluorochrome or a quenching molecule that absorbs energy emitted from the fluorescence donor. The second fluorochrome absorbs the energy that is emitted from the fluorescence donor and emits light of longer wavelength than the light emitted by the fluorescence donor. The quenching molecule absorbs energy emitted by the fluorescence donor.

Any luminescent molecule, preferably a fluorochrome and/or fluorescent quencher may be used in the practice of this invention, including, for example, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 6501665, BODIPY TMR-X, BODIPY TR-X, Dialkylaminocoumarin, Cy5.5, Cy5, Cy3.5, Cy3, DTPA(Eu3+)-AMCA and TTHA(Eu3+)AMCA.

In one embodiment, the 3' terminal nucleotide of the oligonucleotide probe is blocked or rendered incapable of extension by a nucleic acid polymerase. Such blocking is conveniently carried out by the attachment of a reporter or quencher molecule to the terminal 3' position of the probe.

In another embodiment, reporter molecules are fluorescent organic dyes derivatized for attachment to the terminal 3' or terminal 5' ends of the probe via a linking moiety. Preferably, quencher molecules are also organic dyes, which may or may not be fluorescent, depending on the embodiment of the invention. For example, in a preferred embodiment of the invention, the quencher molecule is non-fluorescent. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

In one embodiment, reporter and quencher molecules are selected from fluorescein and non-fluorescent quencher dyes.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink. II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

Rhodamine and non-fluorescent quencher dyes are also conveniently attached to the 3' end of an oligonucleotide at the beginning of solid phase synthesis, e.g., Woo et al., U.S. Pat. No. 5,231,191; and Hobbs, Jr., U.S. Pat. No. 4,997,928.

Attachment of a CataCleave Probe to a Solid Support

In certain embodiments of the invention, the oligonucleotide probe can be attached to a solid support. Different probes may be attached to the solid support and may be used to simultaneously detect different target sequences in a sample. Reporter molecules having different fluorescence wavelengths can be used on the different probes, thus enabling hybridization to the different probes to be separately detected.

Examples of preferred types of solid supports for immobilization of the oligonucleotide probe include polystyrene, avidin coated polystyrene beads cellulose, nylon, acrylamide gel and activated dextran, controlled pore glass (CPG), glass plates and highly cross-linked polystyrene. These solid supports are preferred for hybridization and diagnostic studies because of their chemical stability, ease of functionalization and well defined surface area. Solid supports such as controlled pore glass (500 Å, 1000 Å) and non-swelling high cross-linked polystyrene (1000 Å) are particularly preferred in view of their compatibility with oligonucleotide synthesis.

The oligonucleotide probe may be present in a free form in a reaction solution. Alternatively, the oligonucleotide probe may be attached to the solid support in a variety of manners. For example, the probe may be attached to the solid support by attachment of the 3' or 5' terminal nucleotide of the probe to the solid support. However, the probe may be attached to the solid support by a linker which serves to distance the probe from the solid support. The linker is most preferably at least 30 atoms in length, more preferably at least 50 atoms in length.

Hybridization of a probe immobilized to a solid support generally requires that the probe be separated from the solid support by at least 30 atoms, more-preferably at least 50 atoms. In order to achieve this separation, the linker generally includes a spacer positioned between the linker and the 3' nucleoside. For oligonucleotide synthesis, the linker arm is usually attached to the 3'-OH of the 3' nucleoside by an ester linkage which can be cleaved with basic reagents to free the oligonucleotide from the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred because it is commercially available, soluble in both organic and aqueous media, easy to functionalize, and is completely stable under oligonucleotide synthesis and post-synthesis conditions.

The linkages between the solid support, the linker and the probe are preferably not cleaved during removal of base protecting groups under basic conditions at high temperature. Examples of preferred linkages include carbamate and amide linkages. Immobilization of a probe is well known in the art and one skilled in the art may determine the immobilization conditions.

According to one embodiment of the method, the hybridization probe is immobilized on a solid support. The oligonucleotide probe is contacted with a sample of nucleic acids under conditions favorable for hybridization. In an unhybridized state, the fluorescent label is quenched by the quencher. On hybridization to the target, the fluorescent label is separated from the quencher resulting in fluorescence.

Immobilization of the hybridization probe to the solid support also enables the target sequence hybridized to the probe to be readily isolated from the sample. In later steps, the isolated target sequence may be separated from the solid support and processed (e.g., purified, amplified) according to methods well known in the art depending on the particular needs of the researcher.

Real-Time Detection of Target Nucleic Acid Sequences Using a CataCleave Probe

Figure 2:
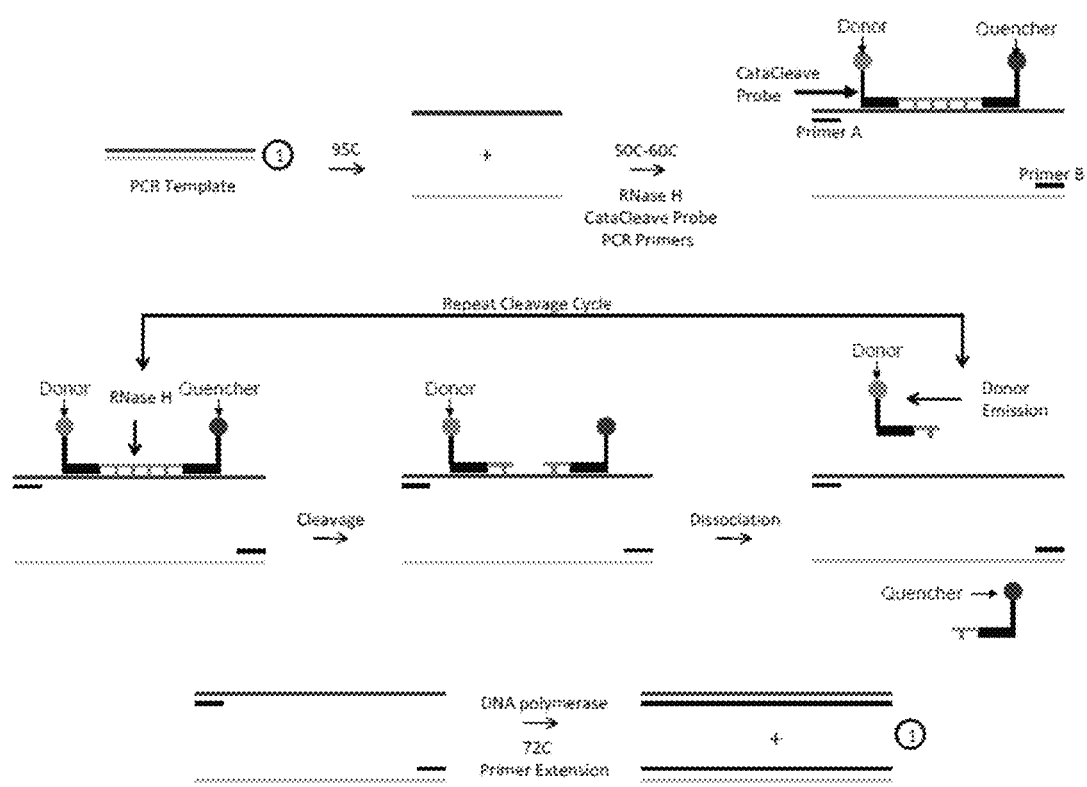
FIG. 2 is a schematic representation of a method for real-time monitoring nucleic acid amplification using a CATACLEAVE™ probe which is degraded by an endonuclease.

The labeled oligonucleotide probe may be used as a probe for the real-time detection of a target nucleic acid sequence in a sample (see FIGS. 1 and 2).

A CataCleave oligonucleotide probe is first synthesized with DNA and RNA sequences that are complimentary to sequences found within a PCR amplicon comprising a selected target sequence. In one embodiment, the probe is labeled with a FRET pair, for example, a fluorescein molecule at one end of the probe and a non-fluorescent quencher molecule at the other end.

Real-time nucleic acid amplification is then performed on a target polynucleotide in the presence of a thermostable nucleic acid polymerases, a thermostable modified RNase H activity, a pair of PCR amplification primers capable of hybridizing to the target polynucleotide, and a labeled CataCleave oligonucleotide probe. For the detection of a target RNA sequence, the reaction mix includes a reverse transcriptase activity for an initial cDNA synthesis step as described herein. During the real-time PCR reaction, hybridization of the probe with the PCR amplicons forms a RNA:DNA heteroduplex that can be cleaved by an RNase H activity. Cleavage of the probe by RNase H leads to the separation of the fluorescent donor from the fluorescent quencher and results in the real-time increase in fluorescence of the probe corresponding to the real-time detection of the target DNA sequences in the sample.

In certain embodiments, the real-time nucleic acid amplification permits the real-time detection of a single target DNA molecule in less than about 40 PCR amplification cycles.

Kits

The disclosure herein also provides for a kit format which comprises a package unit having one or more reagents for the real-time detection of target nucleic acid sequences in a sample. The kit may also contain one or more of the following items: buffers, instructions, and positive or negative controls. Kits may include containers of reagents mixed together in suitable proportions for performing the methods described herein. Reagent containers preferably contain reagents in unit quantities that obviate measuring steps when performing the subject methods.

Kits may also contain reagents for real-time PCR including, but not limited to, a thermostable polymerases, thermostable modified RNase H, primers selected to amplify a nucleic acid target sequence and a labeled CataCleave oligonucleotide probe that anneals to the real-time PCR product and allows for the detection of the target nucleic acid sequences according to the methodology described herein. Kits may comprise reagents for the detection of two or more target nucleic acid sequences. In another embodiment, the kit reagents further comprised reagents for the extraction of genomic DNA or RNA from a biological sample. Kit reagents may also include reagents for reverse transcriptase-PCR analysis where applicable.

EXAMPLES

The following examples set forth methods for using the modified RNAse H enzyme composition according to the present invention. It is understood that the steps of the methods described in these examples are not intended to be limiting. Further objectives and advantages of the present invention other than those set forth above will become apparent from the examples which are not intended to limit the scope of the present invention.

Example 1

Pfu RNase HII Cleavage Assays

The qualitative cleavage activity of Pfu RNase HII was examined where the amount of Pfu in the reaction was held constant while the probe:template ratio was varied. Activity was also examined where the probe:template ratio was held constant while the amount of Pfu in the reaction was varied.

The amino acid sequence of Pfu RNase HII is SEQ ID NO: 1 and reproduced below.

```
                                                            (SEQ ID: 1)
MKIGGIDEAG  RGPAIGPLVV  ATVVVDEKNI  EKLRNIGVKD  SKQLTPHERK  NLFSQITSIA   60

DDYKIVIVSP  EEIDNRSGTM  NELEVEKFAL  ALNSLQIKPA  LIYADAADVD  ANRFASLIER  120

RLNYKAKIIA  EHKADAKYPV  VSAASILAKV  VRDEEIEKLK  KQYGDFGSGY  PSDPKTKKWL  180

EEYYKKHNSF  PPIVRRTWET  VRKIEESIKA  KKSQLTLDKF  FKKP                   224
```

Figure 11A:
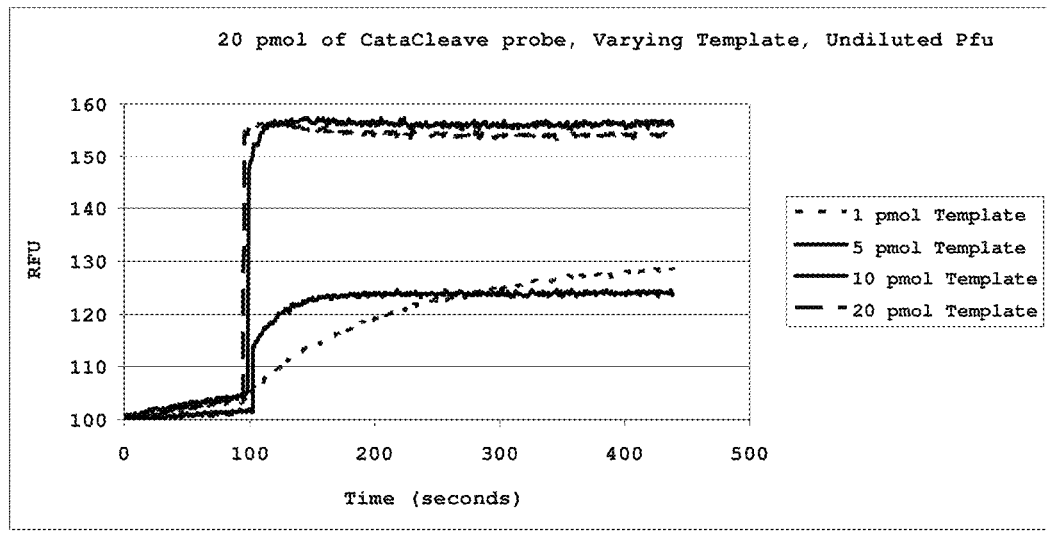
FIGS. 11A and 11B depict graphs showing a determination of RNase HII activity, as described in Example 1.
Figure 11B:
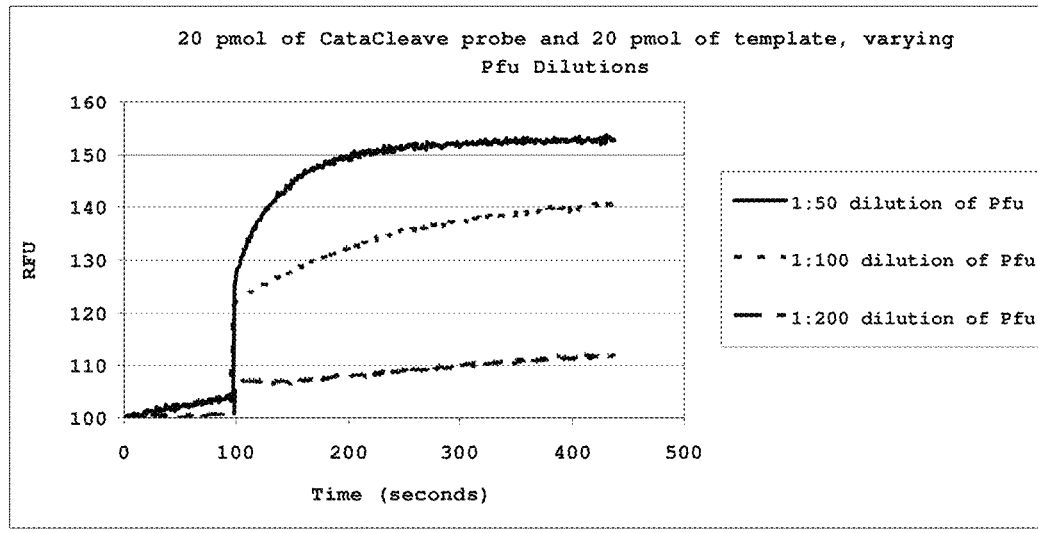

Pfu RNase HII activity was measured as follows. Reaction mixtures each containing 30 µl of 10× reaction buffer, 20 pmol of probe, varying pmol of template, and H$_2$O to 300 µl were incubated at 64° C. for 10 minutes, then 1 µl of Pfu RNase HII was added. The reaction buffer, probe, and template compositions are described in Example 2, below. Cleavage of the fluorescein-labeled probe by Pfu RNase HII was monitored by fluorescence emission at 520 nm (upon excitation at 490 nm). Results are shown in FIG. 11A. The results in FIG. 11A show that as the probe:template ratio is increased the reaction rates increased. At a 20:20 pmol ratio the reaction is instant, meaning that the Pfu RNase HII is in great excess over the substrates. Having determined that this ratio is correctly set, experiments were performed with different concentrations of Pfu. The results are shown in FIG. 11B. Pfu RNase HII was diluted into 1× reaction buffer. As the Pfu RNase HII is diluted, cleavage activity decreased. At a dilution of 1:200 the rate was linear with time.

Example 2

Reversible Formaldehyde Crosslinking of Pfu RNase HII

Pfu RNase HII was subjected to formaldehyde crosslinking using various concentrations of formaldehyde.

The following buffering agents were used.

Crosslinking Buffer: 20 mM HEPES, pH 7.9, 200 mM KCl, and 1 mM EDTA

2× RNase HII Storage Buffer: 100 mM Tris-HCl, pH 8.0, 200 mM NaCl, and 0.2 mM EDTA 25 µL of 25 mg/mL (about 50 OD) Pfu RNase HII was diluted with 475 µL of the crosslinking buffer (1.25 mg/mL, about 2.5 OD). The Pfu RNase HII was subject to crosslinking reactions on ice under the following conditions:

| Pfu Crosslinking Conditions | 1.25 mg/mL Pfu RNase HII (ul) | H2O (ul) | 13.8% Formaldehyde in H2O (made fresh) (ul) | Total Volume (ul) | % Formaldehyde (Final) |
|---|---|---|---|---|---|
| 1 | 10 | 8.00 | 0.00 | 18 | 0.00 |
| 2 | 10 | 7.75 | 0.25 | 18 | 0.19 |
| 3 | 10 | 7.50 | 0.50 | 18 | 0.38 |
| 4 | 10 | 7.25 | 0.75 | 18 | 0.58 |
| 5 | 10 | 7.00 | 1.00 | 18 | 0.77 |
| 6 | 10 | 6.00 | 2.00 | 18 | 1.53 |
| 7 | 10 | 4.00 | 4.00 | 18 | 3.07 |
| 8 | 10 | 0.00 | 8.00 | 18 | 6.13 |

Then, the reaction mixtures were incubated in 37° C. water bath for 30 min. The mixtures were placed on ice and 2 µL of 2 M Tris-HCl, pH 8.0 was added to each reaction mixture. After completion of the reaction, the reaction mixture was purified using G50 microspin columns pre-equilibrated with 2× RNase HII Storage Buffer, followed by dilution with an equal volume of glycerol for storage at −20° C. A series of isothermal cleavage reactions were performed to test each crosslinking condition in the table above using the conditions described below. Reactions of type "A" did not contain target complementary to the probe. Reactions of type "C" did not contain any Pfu RNase HII.

|  | Reaction Type | | |
|---|---|---|---|
|  | A | B | C |
| Reaction volume (µL): | 20 | 20 | 20 |
| Crosslinked Pfu (µL): | 1 | 1 | 0 |
| 10x Reaction Buffer | 2 | 2 | 2 |
| 5 µM inv-CC-Probe 1 Probe (SEQ ID NO: 2) | 1 | 1 | 1 |
| 0.1 µM Sal Target Oligo (SEQ ID NO: 3) | 0 | 1 | 1 |
| Ultrapure H2O | 16 | 15 | 16 |

1× Reaction Buffer has the following composition:
32 mM HEPES-KOH, pH 7.8
100 mM potassium acetate
4 mM magnesium acetate
0.11% bovine serum albumin
1% dimethylsulfoxide
4 mM MgCl2
inv-CC Probe 1 Probe had the following sequence:

(SEQ ID NO: 2)
5'-FAM-TCTGGTTGArUrUrUrCCTGATCGCA-Iowa Black FQ-3'

Sal Target Oligo had the following sequence:

(SEQ ID NO: 3)
5'-TGCGATCAGGAAATCAACCAGA-3'

SEQ ID NO: 3 is complementary to SEQ ID NO: 2 and serves as the template to which the probe hybridizes.

RNase HII activity was measured at 50° C. without activation and at 50° C. after 95° C. activation for 15 minutes.

Figure 4:
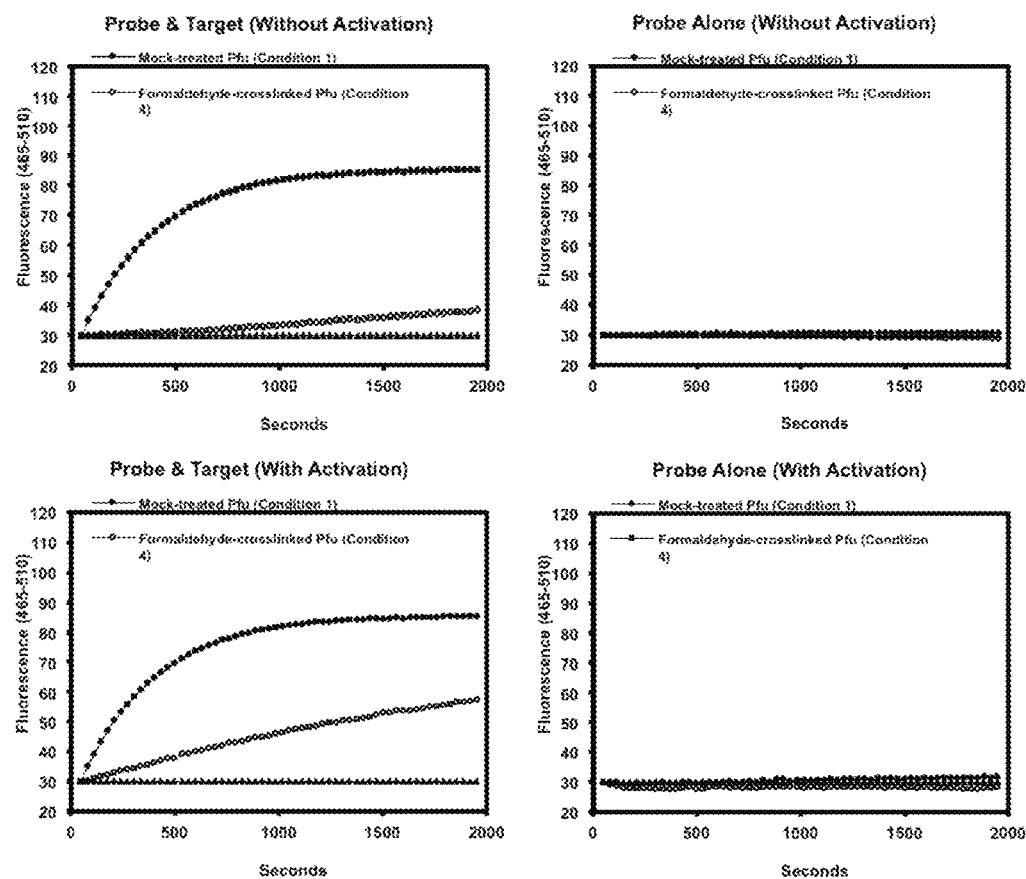

Cleavage of the fluorescein-labeled probe by Pfu RNase HII was monitored by fluorescence emission at 510 nm (upon excitation at 465 nm) at the indicated assay temperature for duration of 0-30 minutes. The results are shown in FIG. 4. Assays in which the Pfu was not reacted with formaldehyde are referred to as "Mock-treated Pfu" and correspond to Pfu crosslinking condition number one in the table above. The results of the experiments demonstrated that Pfu crosslinking condition number four resulted in the greatest degree of inhibition of cleavage activity and greatest recovery of activity after activation at 95° C. and are shown in the figures. FIG. 4A shows that reaction of Pfu with 0.75 ul of 13.8% formaldehyde resulted in the inhibition of Pfu cleavage activity similar to that seen in the absence of enzyme. Activity of the mock treated Pfu sample represents baseline cleavage activity. After activation at 95° C., cleavage activity of the formaldehyde treated Pfu was restored to approximately 50% of the mock treated level as shown in FIG. 4B. FIGS. 4B and 4C demonstrate that probe cleavage did not occur in the absence of template under the assay conditions.

Example 3

Detection of *Salmonella* invA Amplification Using Formaldehyde-Crosslinked RNase HII Performance of formaldehyde-crosslinked Pfu RNase HII was measured using the *Salmonella* invA CataCleave™ PCR assay. Untreated Pfu RNase HII and formaldehyde-crosslinked Pfu RNase HII (Sample #4 in Example 2) were tested for their ability to function in a CATACLEAVE™ PCR assay for detecting 5 to 5×10$^6$ copies of the *Salmonella* invA gene target.

CATACLEAVE™ Master Mix (in µl):

|  | Untreated Pfu (Sample 1) | Hot Star Pfu (Sample 4) |
|---|---|---|
| Number of reactions: | 9 | 9 |
| Reaction volume (µL): | 25 | 25 |
| Sample volume (µL): | 10 | 10 |
| 10x I Buffer w/ 40 mM MgCl2 | 22.5 | 22.5 |
| 2 mM dNTP mix (4 mM dUTP) | 9 | 9 |
| 25 µM inv-CC-Probe2 Probe* | 1.8 | 1.8 |
| 100 µM Salmonella-F1 Primer** | 1.8 | 1.8 |
| 100 µM Sal-InvR2 Primer*** | 1.8 | 1.8 |
| Ultrapure H$_2$O | 88.2 | 88.2 |

-continued

|  | Untreated Pfu (Sample 1) | Hot Star Pfu (Sample 4) |
|---|---|---|
| Uracil DNA N-Glycosylase | 0.9 | 0.9 |
| RNase HII | 4.5 | 4.5 |
| Taq DNA Polymerase | 4.5 | 4.5 |
| total volume of ReadyMix: | 135 | 135 | inv-CC-Probe 2 Probe: 5'-FAM-CGATCAGrGrArArATCAACCAG (SEQ ID NO: 4)-Iowa Black FQ-3',
**Salmonellas-F1 primer: 5'-TCGTCATTCCATTACCTACC (SEQ ID NO: 5)-3',
***Sal-InvR2 Primer: 5'-TACTGATCGATAATGCCAGACGAA (SEQ ID NO: 6)-3'.

Figure 5A:
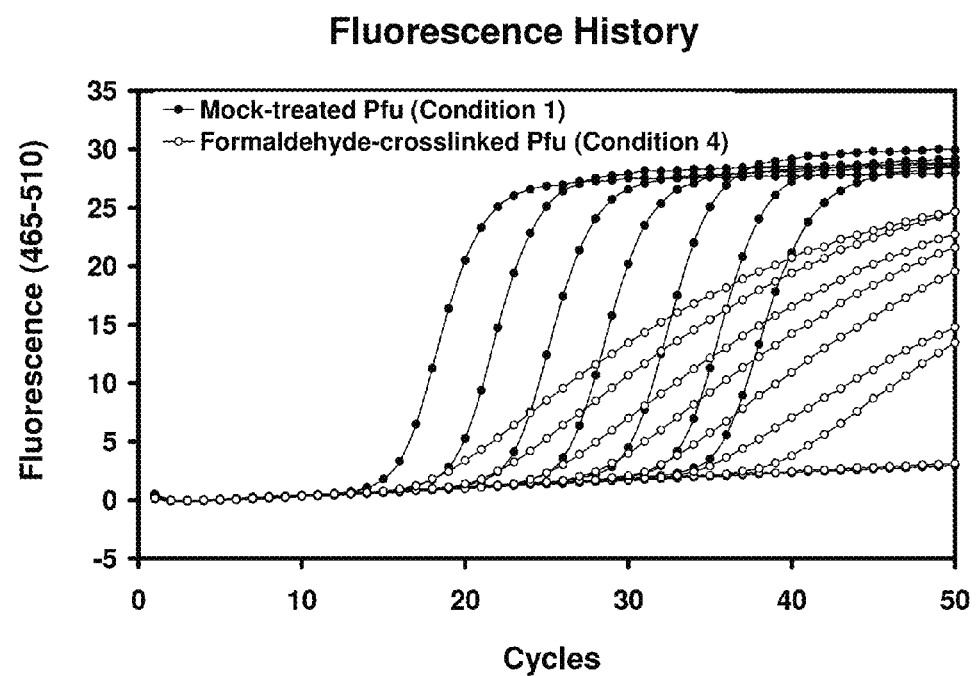
FIGS. 5A and 5B are graphs depicting the performance (fluorescence in FIG. 5A, Cp valued in FIG. 5B) of the reactivated Pfu RNase HII which has been formaldehyde-treated.
Figure 5B:
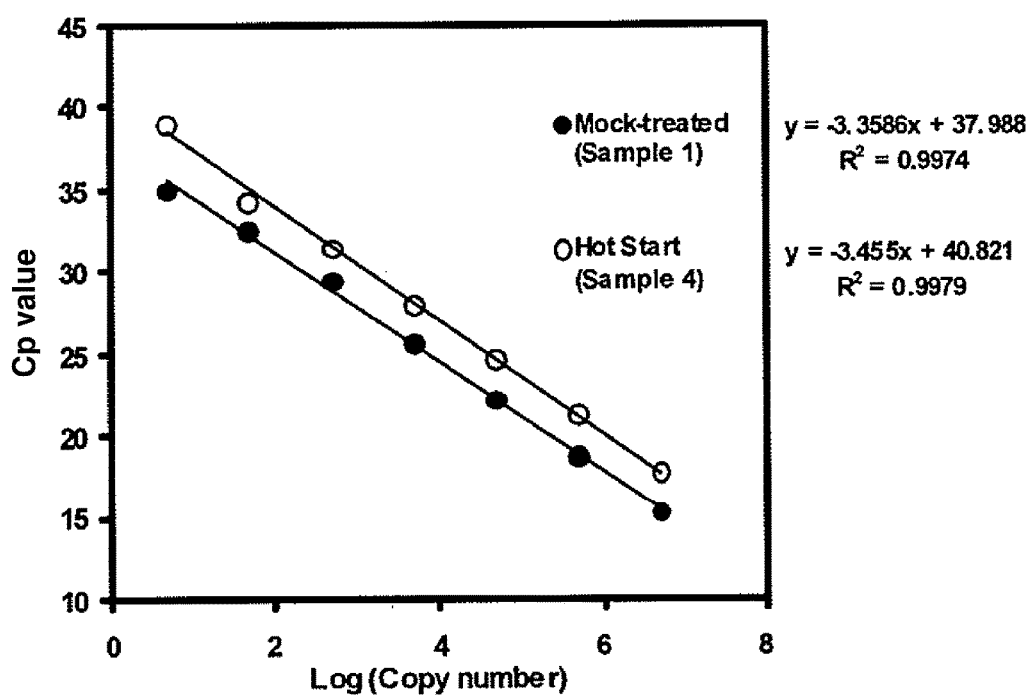

As can be seen from FIGS. 5A and 5B, there is no significant difference between the PCR efficiencies of the untreated Pfu RNase HII ("Mock-treated Pfu" in FIG. 5, sample #1 in Example 2) and the formaldehyde-crosslinked Pfu RNase HII ("Formaldehyde crosslinked Pfu" in FIG. 5, sample #4 in Example 2). Cp values were higher by about 2.5-3 cycles for the formaldehyde-crosslinked RNase HII as compared with the untreated RNase HII. The endpoint fluorescence was also lower for the amplification using formaldehyde-crosslinked RNase HII.

Example 4

Reversible Cis-Aconitylation of Pfu RNase HII

Figure 3:
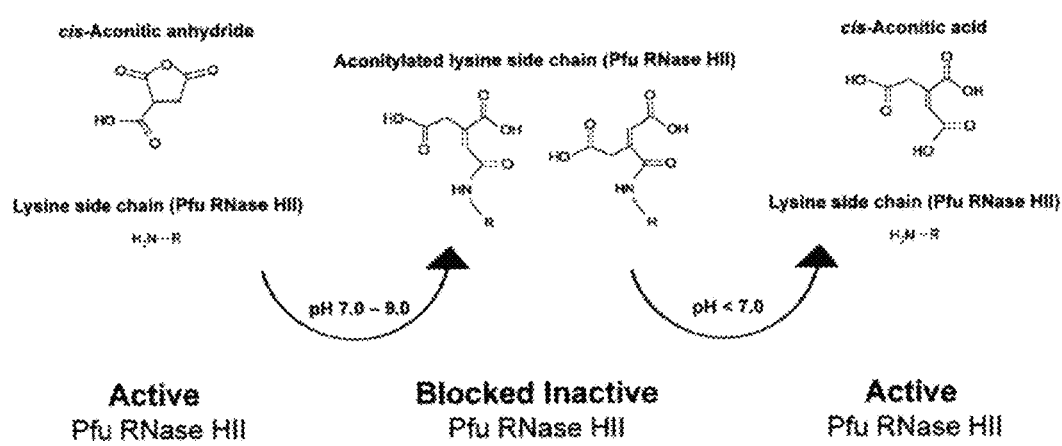
FIG. 3 is a reaction scheme of acylation of RNase HII according to one embodiment, FIG. 4 are graphs showing the activity of the formaldehyde-treated RNase HII, measured at 37° C. and 50° C. without activation and at 60° C. after 95° C. activation as described in Example 2.

Pfu RNase HII was subjected to cis-aconitylation using various concentrations of cis-aconitic anhydride from 50:1 to 200:1 molar ratios of cis-aconitic anhydride to the enzyme (see FIG. 3).

The following buffers were used for the acylation.
2× RNase HII Storage Buffer:
100 mM Tris-HCl, pH 8.0
200 mM NaCl
0.2 mM EDTA
10× Acylation Buffer
500 mM Tris-HCl, pH 7.5
650 mM KCl
10 mM EDTA 25 µL of 25 mg/mL (approximately 50 OD) Pfu RNase HII was diluted with 475 µL of acylation buffer (1.25 mg/mL, approximately 2.5 OD) and acylation reactions were set up on ice. Reaction mixtures were incubated at 4° C. for about 18 hours. Reaction mixtures were purified using G50 microspin columns pre-equilibrated with 2× RNase HII Storage Buffer.

Each reaction mixture was diluted with an equal volume of glycerol for storage at −20° C. The molar ratios of cis-aconitic anhydride and RNase HII and other acylation conditions are shown in Table below.

Then, the endonuclease activity of the cis-aconitylated Pfu RNase HII was determined at 50° C. with and without a heat treatment (reactivation) at 95° C. for 15 minutes. The following RNase HII assay mix was used to measure the RNase HII activity.

| RNase HII Assay master Mix (1) (in µl) | | |
|---|---|---|
|  | A | B |
| Number of reactions: | 20 | 20 |
| Reaction volume (µL): | 20 | 20 |
| Sample volume (µL): | 1 | 1 |
| 5× Tris-Acetate Buffer, pH 8.4 | 80 | 80 |
| 5 µm inv-CC-Probe1 Probe* | 20 | 20 |
| 0.1 µM Sal Target Oligo** | 0 | 20 |
| Ultrapure H₂O | 280 | 260 |
| total volume of ReadyMix: | 380 | 380 |

*inv-CC-Probe1: 5'-FAM-TCTGGTTGArUrUrUrCCTGATCGCA (SEQ ID NO: 2)-Iowa Black FQ-3'
**Sal Target Oligo sequence: 5'-TGCGATCAGGAAATCAACCAGA (SEQ ID NO: 3)-3'

Figure 6A:
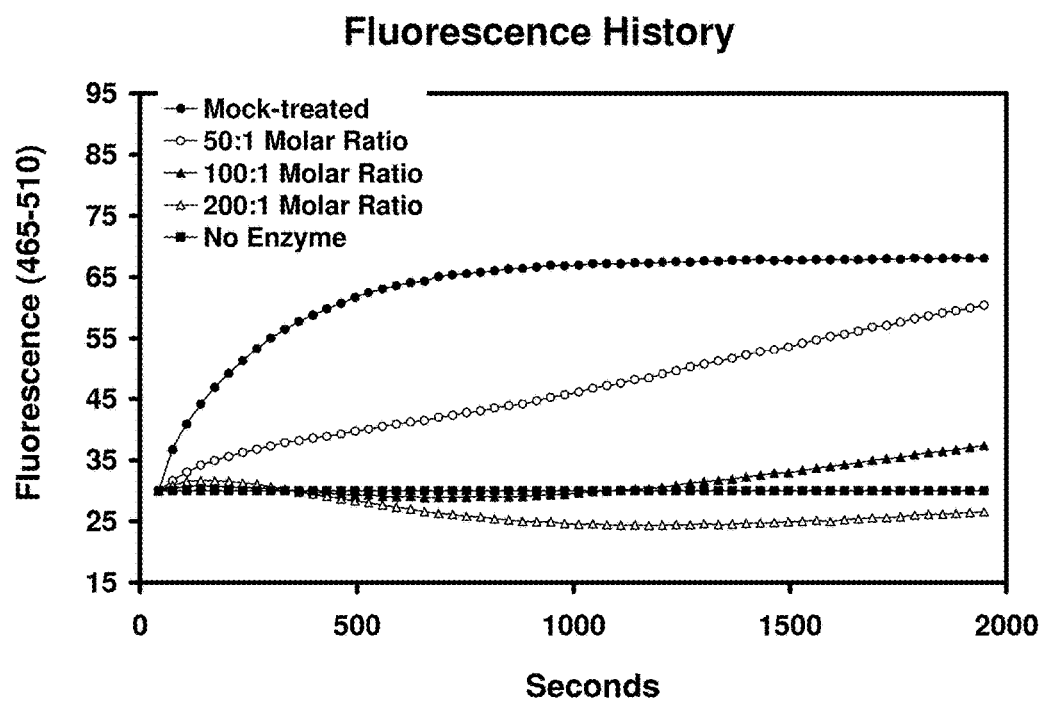
FIGS. 6A and 6B are graphs depicting the activity of reversibly acylated Pfu RNase HII without reactivation (FIG. 6A) and with reactivation (FIG. 6B)
Figure 6B:
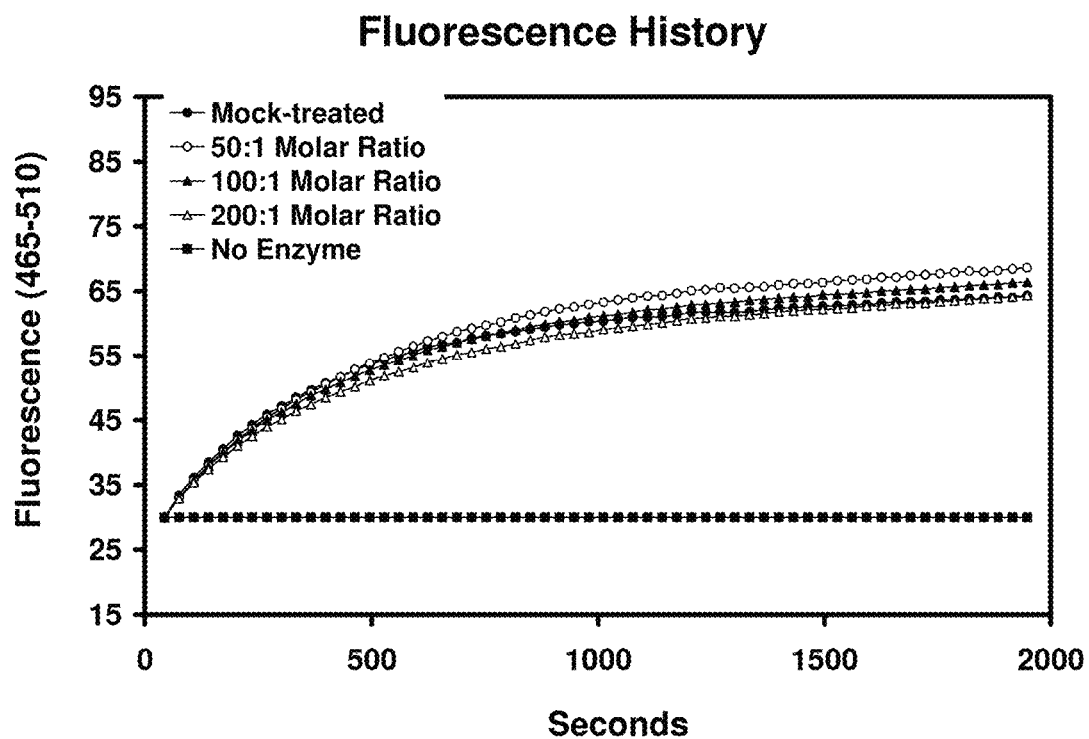

The results are shown in FIG. 6A (without reactivation) and FIG. 6B (with reactivation).

The results show that about 200:1 molar ratio of cis-aconitic anhydride:enzyme is necessary for complete inactivation of RNase HII activity at 50° C. All concentrations of cis-aconitic anhydride used resulted in near full reactivation of RNase HII activity after 15 min at 95° C., when the reactivation (i.e., heating at 95° C.) was performed using Tris acetate, pH 8.4 buffer.

In order to evaluate whether a buffering agent has any impact on the reactivation, the same reactivation procedure was performed using a RNase HII assay master mix (2) which uses 1× reaction buffer (composition described in Example 2).

| RNase HII Assay master Mix (2) (in µl) | | |
|---|---|---|
|  | A | B |
| Number of reactions: | 7 | 7 |
| Reaction volume (µL): | 20 | 20 |
| Sample volume (µL): | 1 | 1 |
| 10× Reaction Buffer w/ 40 mM | 14 | 14 |
| 5 µm inv-CC-Probe 1 Probe | 7 | 7 |
| 0.1 µm Sal Target Oligo | 0 | 7 |
| Ultrapure H₂O | 112 | 105 |
| total volume of ReadyMix: | 133 | 133 |

| Sample # | 1.25 mg/mL Pfu RNase HII (ml) | H2O (ml) | 10× Acylation Buffer (ml) | 10 mg/mL cis-aconitic anhydride in EtOH (made fresh) (ml) | Total Volume (ml) | Molar Ratio (cis-Aconitic anhydride/RNase) |
|---|---|---|---|---|---|---|
| 1 | 10 | 8.00 | 2 | 0.00 | 20 | 0 |
| 2 | 10 | 7.62 | 2 | 0.39 | 20 | 50 |
| 3 | 10 | 7.23 | 2 | 0.77 | 20 | 100 |
| 4 | 10 | 6.46 | 2 | 1.54 | 20 | 200 |

RNase HII activity was measured at 50° C. (60 cycles) for a 30-second hold time for each cycle.

The results (not shown) indicate that reaction buffer, which contains HEPES-KOH pH 7.8 (instead of Tris-HCl), is also capable of reactivation.

Example 5

Detection of *Salmonella* invA Using Acylated RNase HII

Performance of formaldehyde crosslinked Pfu RNase HII (Sample 4 in Example 2) was measured using *Salmonella* invA and CataCleave™ PCR assay. The master mix for amplification was as follows. The assay was performed at pH 8.4 or pH 8.7.

| CATACLEAVE ™ Master Mix (in μl) | | |
|---|---|---|
| | pH 8.4 | pH 8.7 |
| Number of reactions: | 6 | 6 |
| Reaction volume (μL): | 25 | 25 |
| Sample volume (μL): | 10.5 | 10.5 |
| 5x Tris-Acetate Buffer | 30 | 30 |
| 2 mM dNTP mix (4 mM dUTP) | 6 | 6 |
| 25 μm inv-CC-Probe2 Probe* | 1.2 | 1.2 |
| 100 μm Salmonella-F1 Primer** | 1.2 | 1.2 |
| 100 μm Sal-InvR2 Primer*** | 1.2 | 1.2 |
| Ultrapure H₂O | 43.8 | 43.8 |
| Uracil DNA N-Glycosylase | 0.6 | 0.6 |
| Taq DNA Polymerase | 3 | 3 |
| total volume of ReadyMix: | 87 | 87 |

*inv-CC-Probe 2 Probe: 5'-FAM-CGATCAGrGrArArATCAACCAG (SEQ ID NO: 4)-Iowa Black FQ-3'
**Salmonella-F1 primer: 5'-TCGTCATTCCATTACCTACC (SEQ ID NO: 5)-3',
***Sal-InvR2 Primer: 5'-TACTGATCGATAATGCCAGACGAA (SEQ ID NO: 6)-3'.

Figure 7A:
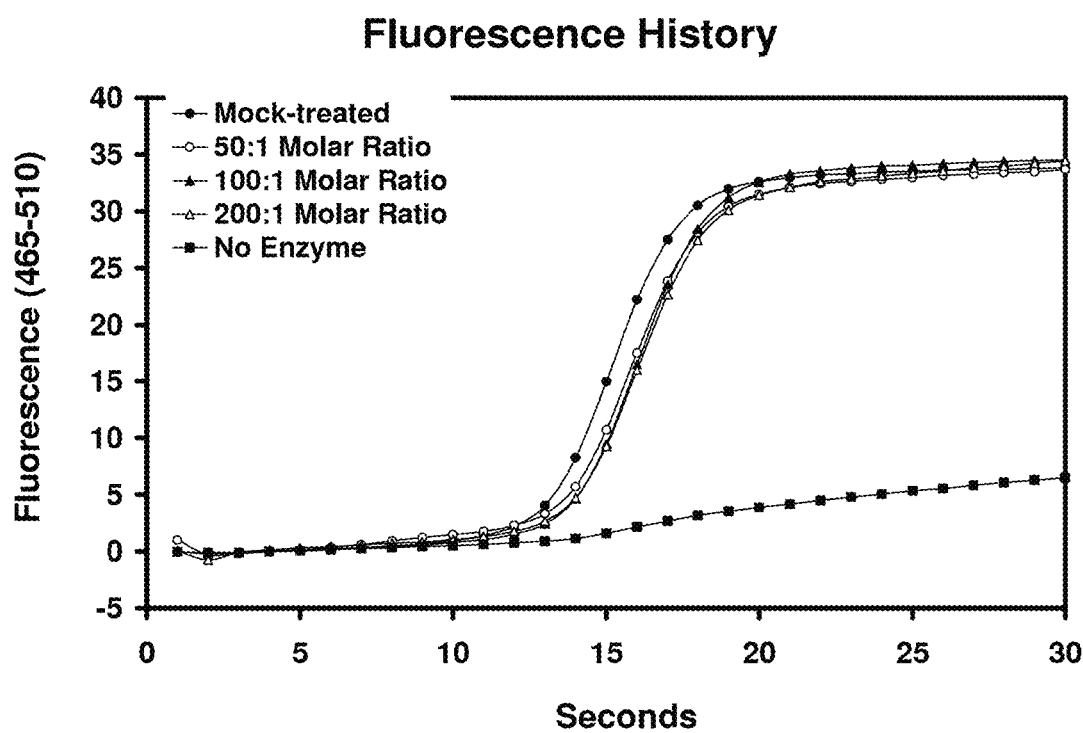
FIGS. 7A and 7B are graphs depicting the activity of reactivated Pfu RNase HII, which has been acylated, at pH 8.4 (FIG. 7A) and 8.7 (FIG. 7B)
Figure 7B:
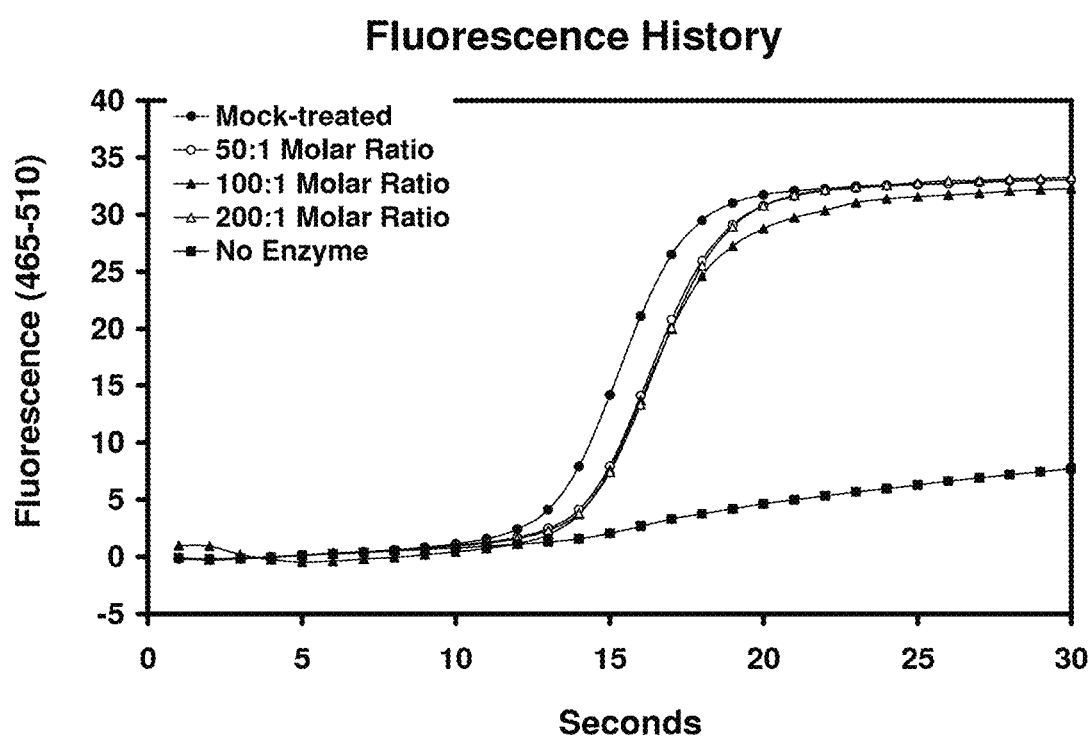

The results of FIG. 7A (at pH 8.4) and FIG. 7B (pH 8.7) demonstrate that using either Tris-acetate buffer (pH 8.4 or 8.7) is adequate to get near full re-activation of the cis-aconitylated Pfu RNase HII in the *Salmonella* invA CATACLEAVE qPCR assay (with a 15 min 95° C. heat treatment).

Also, about 200:1 molar ratio of cis-aconitic anhydride to enzyme seems to be necessary and sufficient for creating a hot-start Pfu RNase HII that functions well in amplification and has minimal RNase H activity without heat activation.

Example 6

One-Step RT PCR Amplification of HIV-1

The reversibly modified RNase HII as described and prepared above may be particularly suitable for use in one-step RT PCR amplification of viral RNA targets. The modified, inactive RNase HII does not cleave target ribonucleic acid molecules in a sample and it allows reverse transcriptase to produce viral cDNA molecules from the RNA nucleic acids.

In the instant exemplary embodiment, the modified RNase HII is used to detect a HIV-1 target RNA. Sample #4 of Example 2 (composition 2) and sample #4 of Example 3 (composition 3) were used as modified RNase HII. For comparison, unmodified Pfu RNase HII were used (composition 1).

```
1 X Tris pH 8.7 Buffer 6
  10 mM Tris base pH 8.7 (w/ acetic acid)
  50 mM KOAc
2.5 mM MgOAc
   1 mM DTT Composition 1. One step RT-PCR Tris 8.7 buffer 6 (unmodified Pfu RNase HII) (in μl)
      1 ul       HIV-1_F11-JO primer* 7.5 uM
      1 ul       HIV-1_R6-JO primer** 7.5 uM
      1 ul       HIV-1_CCProbe5*** 10 uM
      1 ul       dNTP 10 mM each
      5 ul       5 x Tris 8.7 buffer 2****
      1 ul       RT-PCR enzyme mix
      1 ul       Pfu RNase HII
     13 ul       H2O add 24 ul to 1 ul RNA template Composition 2. RT-PCR Tris 8.7 buffer 6 with modified RNase HII of Example 2
(Sample 4) (in μl)
      1 ul       HIV-1_F11-JO primer* 7.5 uM
      1 ul       HIV-1_R6-JO primer** 7.5 uM
      1 ul       HIV-1_CCProbe5*** 10 uM
      1 ul       dNTP 10 mM each
      5 ul       5 x Tris 8.7 buffer 2****
```

```
         1 ul      RT-PCR enzyme mix
         1 ul      Pfu RNase HII (formaldehyde)
        13 ul      H2O add 24 ul to 1 ul RNA template Composition 3. One step RT-PCR Tris 8.7 buffer 6 with modified RNase HII of
Example 3 (Sample 4)
         1 ul      HIV-1_F11-JO primer* 7.5 uM
         1 ul      HIV-1_R6-JO primer** 7.5 uM
         1 ul      HIV-1_CCProbe5*** 10 uM
         1 ul      dNTP 10 mM each
         5 ul      5 x Tris 8.7 buffer 2****
         1 ul      RT-PCR enzyme mix
         1 ul      Pfu RNase HII (cis-aconitic anhydride)
        13 ul      H2O add 24 ul to 1 ul RNA template
*HIV-1-F11-JO: 5'-CCAAGGGGAA GTGACATAGC AGGAACTACT-3', (SEQ ID NO: 7)
**HIV-1_R7-JO: 5'-CTGACGACAGGGCTATACATTCTTACTATTT-3', (SEQ ID NO: 8)
***HIV-1_CCProbe: 5'-FAM-TACCCTTCAGrGrArArCAAATAGGATGGAT-IABlk_FQ-3', (SEQ ID NO: 9)
****Buffer 2: Tris-Acetate pH 8.7, 50 mM KOAc, 2.5 mM MgOAc, and 1 mM DTT.
RT-PCR conditions were as follows:
50° C. 30 min
95° C. 15 min
50 cycles of 95° C. 30 sec, 60° C. 30 sec, and 72° C. 60 sec.
```

The endonuclease activity of RNase HII was measured by following the procedure described in Example 2.

Figure 8:
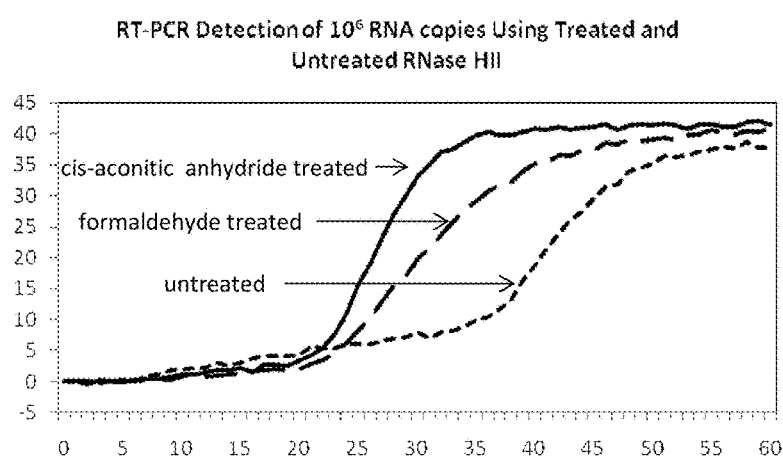
FIG. 8 is a graph depicting the endonuclease activity of untreated RNase HII, and reversibly modified RNase HII, measured on HIV-1 genomic RNA, according to Example 6.

The results are shown in FIG. 8, each show the fluorescence determined on the RT-PCR products using the composition 1, composition 2, and composition 3, respectively. As shown in FIG. 8, the acylated RNase HII showed a steeper curve than that of formaldehyde-crosslinked RNase HII, probably because the acylated RNase HII is reactivated more fully under the conditions used in the Example. Full or complete recovery of activity of formaldehyde treated RNase HII by high temperature incubation is lower than that seen with acylated treated enzyme by changes in pH for equivalent samples.

Example 7

Sensitivity of Reversibly Acylated RNase HII

In order to determine the sensitivity of the modified RNase HII, the same procedure described in Example 6 was followed using the acylated RNase HII (sample #4 of Example 3), except different concentrations of HIV-1 target RNA were present in the amplification composition.

Figure 9:
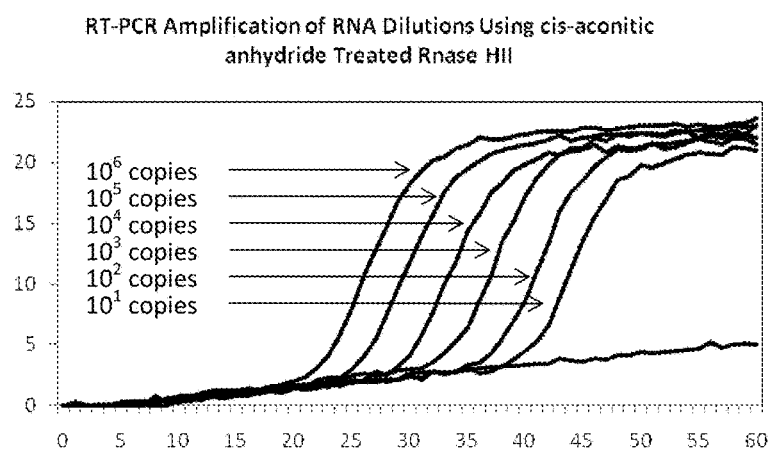
FIG. 9 depicts graphs showing the sensitivity of reversibly acylated Pfu RNase HII for the detection of HIV-1 genomic RNA, as described in Example 7.

The results are shown in FIG. 9. As can be seen in FIG. 9, the one-step RT PCR containing an acylated Pfu RNase H could detect as few as 10 input copies of HIV-1 genomic RNA. No amplification was observed in the negative control. Also, the reactions showed concentration dependence (not shown).

Example 8

Comparison Between Reversibly Acylated RNase HII and Unmodified RNase HII

```
1 X Tris pH 8.7 Buffer 6
 10 mM Tris base pH 8.7 (w/ acetic acid)
 50 mM KOAc
2.5 mM MgOAc
  1 mM DTT
```

```
                       -continued
One step RT-PCR CataCleave buffer 6
   0.5 ul  Salmonella-F1 primer*
   0.5 ul  Sal-invR2 primer **
     1 ul  inv_CCProbe1 5 uM***
     1 ul  dNTP 10 mM each
   2.5 ul  5 x Tris 8.7 buffer 6****
     1 ul  RT-PCR enzyme mix
   0.5 ul  Pfu RNase HII (cis-aconitic anhydride)
    17 ul  H2O add 24 ul to 1 ul RNA template
*Salmonella-F1 primer: 5'-TCGTCATTCCATTACCTACC-3', (SEQ ID NO: 5)
** Sal-invR2 primer: 5'-TACTGATCGATAATGCCAGACGAA-3', (SEQ ID NO: 6)
***inv_CCProbe1:         5'-FAM-TCTGGTTGArUrUrUrCCTGATCGCA-3IABlk_FQ-3', (SEQ ID NO: 2)
****Buffer 6: Tris-Acetate pH8.7, 50 mM KOAc, 2.5 mM MgOAc, 1 mM DTT.
RT-PCR conditions were as follows:
50° C. 30 min
95° C. 15 min
50 cycles of 95° C. 30 sec, 60° C. 30 sec, and 72° C. 60 sec.
```

*Salmonella* invA RNA of about 1500 nucleotides was synthesized using a T7/polymerase system. The RNA was quantified and standardized by copy numbers into pre-aliquoted dilutions of, $10^6$, $10^5$, $10^4$, $10^3$, $10^2$, and 10 copies/W. These dilutions were stored at about −80° C. until use.

One-step RT-PCR amplification compositions (as shown above "one step Reverse Transcriptase-PCR CATA-CLEAVE™ buffer 6") each containing $10^6$, $10^5$, $10^4$, $10^3$, $10^2$, and 10 copies invA RNA/µl were subjected to RT-PCR under the following conditions, and then fluorescence (465-510 nm) of the resulting amplification product was measured. As an acylated Pfu RNase HII, sample #4 of Example 3 was employed. For a comparison, the same amplification composition, which contains an unmodified Pfu RNase HII, rather than the acylated Pfu RNase HII of Example 3 (Sample #4), was used. Results are shown in FIG. 10.

Figure 10:
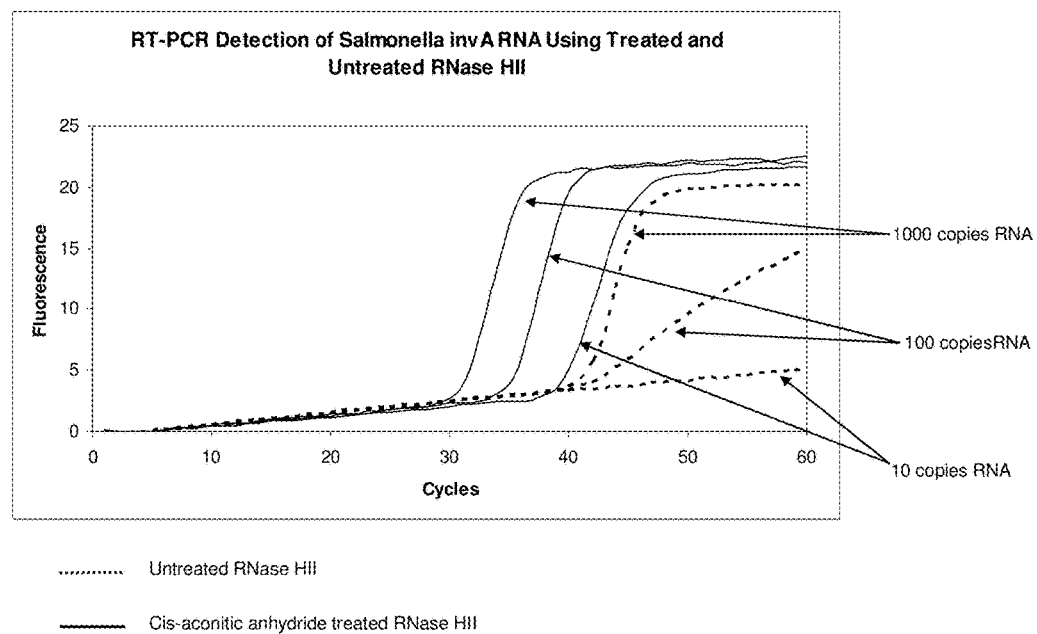
FIG. 10 depicts graphs showing the detection of Salmonella invA RNA using unmodified Pfu RNase HII and reversibly acylated RNase HII.

As can be seen in FIG. 10, the composition containing the acylated RNase HII was able to detect as few as 10 copies of *Salmonella* RNA target nucleic acid having about 1500 nucleotides. When untreated Pfu RNase HII was used, a large Cp shift (about 10 cycles) and loss of sensitivity (1-2 orders of magnitude) were observed. This experiment demonstrated that if the RT reaction is performed in the presence of active RNase HII, that sensitivity is decreased probably due to degradation of the RNA template. This is manifested as a marked increase in Cp values for the real-time reaction.

Any patent, patent application, publication, or other disclosure material identified in the specification is hereby incorporated by reference herein in its entirety. Any material, or portion thereof, that is the to be incorporated by reference herein, but which conflicts with existing definitions, statements, or other disclosure material set forth herein is only incorporated to the extent that no conflict arises between that incorporated material and the present disclosure material.

What is claimed:

1. A method of amplifying a target deoxynucleic acid (DNA) sequence in a sample, comprising
providing an amplification reaction mixture comprising:
a sample comprising the target DNA sequence;
a hot start enzyme composition, comprising DNA polymerase and an enzyme having an inducible RNase H activity, wherein said enzyme is reversibly modified with cis-aconitic anhydride or formaldehyde;
a first primer comprising a sequence complementary to the 5' end of the target DNA sequence;
a second primer comprising a sequence complementary to the 3' end of the target DNA sequence; and
a probe which contains a detectable label and comprises a cleavage sequence of the RNase H;

subjecting the amplification reaction mixture to at least one amplification reaction to form at least one amplification product, and
measuring the detectable label of the resulting amplification product,
wherein the amplification reaction comprises a step of
forming a RNA:DNA duplex by allowing the probe to hybridize to a single strand target DNA sequence; and
heating the reaction mixture to a temperature of about 90° C. or higher,
wherein an activation of the inducible RNase H activity of the enzyme cleaves the cleavage sequence of the probe of the RNA:DNA duplex, wherein the cleavage of the cleavage sequence of the RNA:DNA duplex results the label of the probe to become detectable.

2. The method of claim 1, wherein the step of heating the amplification reaction mixture is conducted at about 95° C.

3. The method of claim 1, wherein the probe is an oligonucleotide comprising one or more DNA sequence portions and a RNA sequence portion, wherein the RNA portion is disposed between two DNA sequences in a way that 3' end and 5' end of the RNA sequence is coupled to each of the two DNA sequences.

4. The method of claim 1, wherein said RNase H activity is heat-inducible.

5. The method of claim 1, wherein said RNase H activity is inducible by modifying the pH of a solution containing the enzyme.

6. The method of claim 1, wherein the formaldehyde is a solution containing formaldehyde at concentration of about 0.2-1% (w/v).

7. The method of claim 1, wherein the enzyme is completely inactivated at 50° C.

8. A method for detecting a target ribonucleic acid (RNA) sequence in a sample, comprising
providing an amplification reaction mixture, wherein the amplification reaction mixture comprises:
a sample containing a target RNA sequence,
a hot start enzyme composition, comprising reverse transcriptase, DNA polymerase and an enzyme having an inducible RNase H activity, wherein said enzyme is reversibly modified with cis-aconitic anhydride or formaldehyde;
a first primer comprising a sequence complementary to the 5' end of a complementary DNA (cDNA) sequence of the target RNA sequence;
a second primer comprising a sequence complementary to the 3' end of the cDNA sequence of the target RNA; and
a probe sequence which contains a detectable label and comprises a cleavage sequence of the RNase H;
initiating reverse transcription of the target RNA sequence to form a cDNA strand of the target RNA;
initiating at least one amplification reaction to form at least one amplification product; and
measuring a signal of the detectable label of the resulting amplification product,
wherein the amplification reaction comprises
allowing the probe to hybridize to the amplification product to form a RNA:DNA duplex; and
heating the amplification reaction mixture to a temperature of about 90° C. or higher, and
wherein an activation of the inducible RNase H activity of the enzyme cleaves the cleavage sequence of the probe of the RNA:DNA duplex, resulting in the label of the probe to become detectable.

9. The method of claim 8, wherein the probe is an oligonucleotide comprising one or more DNA sequence portions and a RNA sequence portion, wherein the RNA portion is disposed between two DNA sequences in a way that 3' end and 5' end of the RNA sequence is coupled to each of the two DNA sequences.

10. The method of claim 8, wherein the target ribonucleic acid sequence is a retrovirus.

11. The method of claim 8, wherein the step of heating the amplification reaction mixture is conducted at about 95° C.

12. The method of claim 8, wherein said RNase H activity is heat-inducible.

13. The method of claim 8, wherein said RNase H activity is inducible by modifying the pH of a solution containing the enzyme.

14. The method of claim 8, wherein the formaldehyde is a solution containing formaldehyde at concentration of about 0.2-1% (w/v).

15. The method of claim 8, wherein the enzyme is completely inactivated at 50° C.

16. A method for detecting target ribonucleic acid (RNA) sequences in a plurality of samples, comprising
providing a microarray having a plurality of amplification reaction mixtures, each amplification reaction mixture comprising:
a sample containing a target RNA sequence,
a hot start enzyme composition, comprising reverse transcriptase, DNA polymerase and an enzyme having an inducible RNase H activity, wherein said enzyme is reversibly modified with cis-aconitic anhydride or formaldehyde;
a first primer comprising a sequence complementary to the 5' end of a cDNA sequence of the target RNA sequence;
a second primer comprising a sequence complementary to the 3' end of the cDNA sequence of the target RNA sequence; and
a probe sequence which contains a detectable label and comprises a cleavage sequence of the RNase H;
and for each amplification reaction mixture in the microarray:
initiating reverse transcription of the target RNA sequence to form a cDNA of the target RNA;
initiating at least one amplification reaction to form at least one amplification product, and
measuring a signal of the detectable label of the resulting amplification product,
wherein the amplification reaction comprises a step of:
allowing the probe to hybridize to the amplification product to form an RNA:DNA duplex; and
heating the amplification reaction mixture to a temperature of about 90° C. or higher,
wherein an activation of the inducible RNase H activity of the enzyme cleaves the cleavage sequence of the probe of the RNA:DNA duplex, wherein the cleavage of the cleavage sequence of the RNA:DNA duplex results the label of the probe to become detectable.

17. The method of claim 16, wherein the target ribonucleic acid sequence is a retrovirus.

18. The method of claim 16, wherein the step of heating the amplification reaction mixture is conducted at about 95° C.

19. The method of claim 16, wherein said RNase H activity is heat-inducible.

20. The method of claim 16, wherein said RNase H activity is inducible by modifying the pH of a solution containing the enzyme.

21. The method of claim 16, wherein the enzyme is completely inactivated at 50° C.

* * * * *